(12) United States Patent
Chepuri et al.

(10) Patent No.: US 9,663,548 B2
(45) Date of Patent: May 30, 2017

(54) 10-α/β-D-ARABINOFURANOSYL-UNDECENES AS POTENTIAL ANTI-MYCOBACTERIAL AGENTS AND PROCESS FOR THE PREPARATION THEREOF

(75) Inventors: Ramana Venkata Chepuri, Pune (IN); Dhiman Sarkar, Maharashtra (IN); Rahul Shivaji Patil, Pune (IN); Sampa Sarkar, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 187 days.

(21) Appl. No.: 14/343,486

(22) PCT Filed: Sep. 14, 2012

(86) PCT No.: PCT/IN2012/000617
§ 371 (c)(1),
(2), (4) Date: May 28, 2015

(87) PCT Pub. No.: WO2013/038430
PCT Pub. Date: Mar. 21, 2013

(65) Prior Publication Data
US 2015/0259372 A1    Sep. 17, 2015

(30) Foreign Application Priority Data
Sep. 14, 2011    (IN) .......................... 2655/DEL/2011

(51) Int. Cl.
*C07H 15/26*    (2006.01)
*C07D 307/20*    (2006.01)
*C07D 493/04*    (2006.01)

(52) U.S. Cl.
CPC ........... *C07H 15/26* (2013.01); *C07D 307/20* (2013.01); *C07D 493/04* (2013.01)

(58) Field of Classification Search
CPC ..... C07H 15/26; C07D 493/04; C07D 307/20
USPC ............ 514/25, 473; 536/4.1, 18.5; 549/476
See application file for complete search history.

(56) References Cited

U.S. PATENT DOCUMENTS

2008/0015344 A1    1/2008    Fraser-Reid et al.

OTHER PUBLICATIONS

Ramana, C.V. et al, Synthesis, 2008, 11, 1783-87.*
"International Application No. PCT/IN2012/000617, International Search Report mailed Dec. 21, 2012", (Dec. 21, 2012), 4 pgs.
Ayers, Benjamin, et al., "Stereoselective synthesis of beta-arabino glycosyl sulfones as potential inhibitors of mycobacterial cell wall biosynthesis.", Carbohydr Res., 344(6), (Apr. 21, 2009), 739-46.
Brennan, P. J., "Structure, function, and biogenesis of the cell wall of *Mycobacterium tuberculosis*", Tuberculosis, 83(1-3), (2003), 91-7.
Callam, Christopher S., et al., "Synthesis and conformational investigation of methyl 4a-carba-D-arabinofuranosides", J Org Chem., 66(26), (Dec. 28, 2001), 8961-72.
Centrone, Charla A., et al., "An efficient route for the synthesis of glycosyl phosphinic acids", J Org Chem., 68(21), (Oct. 17, 2003), 8115-9.
Centrone, Charla A, et al., "Sulfone and phosphinic acid analogs of decaprenolphosphoarabinose as potential anti-tuberculosis agents", Bioorg Med Chem., 12(21), (Nov. 1, 2004), 5495-503.
Centrone, Charla A., et al., "Synthesis and antituberculosis activity of C-phosphonate analogues of decaprenolphosphoarabinose, a key intermediate in the biosynthesis of mycobacterial arabinogalactan and lipoarabinomannan", J Org Chem., 67(25), (Dec. 13, 2002), 8862-70.
Daffe, M., et al., "The envelope layers of mycobacteria with reference to their pathogenicity", Adv Microb Physiol., 39, (1998), 131-203.
Han, Jeongseok, et al., "Synthesis of octyl arabinofuranosides as substrates for mycobacterial arabinosyltransferases", Carbohydr Res., 338(7), (Mar. 28, 2003), 581-8.
Mikusova, Katarina, et al., "Biogenesis of the mycobacterial cell wall and the site of action of ethambutol", Antimicrob Agents Chemother., 39(11), (Nov. 1995), 2484-9.
Pathak, Ashish K., et al., "Synthesis of deoxygenated alpha(1-->5)-linked arabinofuranose disaccharides as substrates and inhibitors of arabinosyltransferases of *Mycobacterium tuberculosis*", Bioorg Med Chem., 17(2), (Jan. 15, 2009), 872-81.
Ramana, C. V., et al., "Stereoselective Synthesis of b-C-Allyl- and b-C-Propargyl-D-arabinofuranosides", Synthesis (11). pp. 1783-1787, (2008), 1783-1787.
Reynolds, R. C, et al., "Ethambutol-sugar hybrids as potential inhibitors of mycobacterial cell-wall biosynthesis", Carbohydr Res., 317(1-4), (Apr. 30, 1999), 164-79.
Sanki, Aditya K., et al., "Synthesis of methyl 5-S-alkyl-5-thio-D-arabinofuranosides and evaluation of their antimycobacterial activity", Bioorg Med Chem., 16(10), (May 15, 2008), 5672-82.
Tam, Pui-Hang, et al., "Recent advances in mycobacterial cell wall glycan biosynthesis", Curr Opin Chem Biol., 13(5-6), (Dec. 2009), 618-25.

* cited by examiner

*Primary Examiner* — Ganapathy Krishnan
(74) *Attorney, Agent, or Firm* — Schwegman Lundberg & Woessner, P.A.

(57) ABSTRACT

Disclosed herein is 10-α/β-D-Arabinofuranosylundecenes of general Formula (II) or pharmaceutically acceptable salts thereof as anti-mycobacterial agents in vitro; (II) wherein R, R1 and R" are as defined herein in the specification. The present invention also discloses a simple stereoselective synthesis 10-α/β-D-Arabinofuranosylundecenes of Formula (II) to target enzymes involved in the biosynthesis of cell wall of *Mycobacterium* and thus useful as inhibitors in the *Mycobacterium tuberculosis* drug development.

13 Claims, 6 Drawing Sheets

10-α/β-D-ARABINOFURANOSYL-UNDECENES AS POTENTIAL ANTI-MYCOBACTERIAL AGENTS AND PROCESS FOR THE PREPARATION THEREOF

PRIORITY CLAIM TO RELATED APPLICATIONS

This application is a national stage application under 35 U.S.C. §371 of PCT/IN2012/000617, filed Sep. 14, 2012, and published as WO 2013/038430 on Mar. 21, 2013, which claims priority to Indian Application No. 2655/DEL/2011, filed Sep. 14, 2011, which applications and publication are incorporated by reference as if reproduced herein and made a part hereof in their entirety, and the benefit of priority of each of which is claimed herein.

TECHNICAL FIELD OF INVENTION

The present invention relates to 10-α/β-D-arabinofuranosyl-undecenes as anti-mycobacterial agents in vitro. The present invention also discloses a simple stereoselective synthesis of 10-undecenyl alpha and beta C-arabinofuranosides to target enzymes involved in the biosynthesis of cell wall of *Mycobacterium* and thus useful as inhibitors in the *Mycobacterium tuberculosis* drug development.

BACKGROUND OF THE INVENTION

Tuberculosis (TB) caused by *Mycobacterium tuberculosis* remains a leading cause of mortality worldwide into 21st century. Tuberculosis is a respiratory transmitted disease affecting nearly 32% of the world's population, more than any other infectious disease. The mortality and spread of this disease has further been aggravated because of synergy of this disease with HIV. Approximately 50% of India's population is reported to be tuberculin test positive and one person dies from TB every minute.

Chemotherapy of tuberculosis started in early forties and since then a number of anti-tubercular agents have been discovered including para-aminosalicylic acid (PAS), isoniazid (INH), pyrazinamide (PZA), cycloserine, ethionamide, rifampicin (RMP), and ethambutol. Strategies have been devised to treat TB from time to time and current treatment involves a combination therapy that extends for months at a time, and the pharmacology of these treatment regimens can be complex. Moreover, a number of anti-TB drugs are found to be ineffective against the disease because of development of resistance strains.

The initial lack of understanding of drug action because of ignorance in the biochemistry of the *Mycobacterium* and the difficulty in manipulating *M. tuberculosis* had hindered efforts to define the mode of action of these agents. Based on the recent developments in evaluating the fine structure and biochemistry of *Mycobacterium bacilli*, it is observed that the cell wall of *Mycobacterium* plays a key role in growth and survival of *Mycobacterium tuberculi* (Mtb). The cell wall in *M. tuberculosis* being very complex and of very poor permeability, contributes significantly to the resistance against many therapeutic agents and for the long life in human lungs. [(a) Tam, P.-H.; Lowary, T. L., Curr. Opin. Chem. Biol. 2009, 13, 618-625; (b) P. J. Brennan, Tuberculosis, 2003, 83, 91-97; (c) M. Daffe and P. Draper, in Adv. Microb. Physiol. 1998, 131-203].

The major portion of the cell wall of Mtb is made up of the polysaccharides arabinogalactan (AG) and lipoarabinomannan (LAM). The AG and LAM polysaccharides are composed of arabinose and are synthesized inside the infected host cells. Arabinan component present in the polysaccharide contains approx 70 arabinofuranose residues. A key structural motif in this arabinan is the hexasaccharide, which is found at the non-reducing ends of both polymers. Mycobacterial viability is critically dependent upon its ability to produce both polysaccharides.

Since arabinose is foreign to the mammalian cells, the inhibition of the corresponding enzymes arabinosyltransferases (AraTs) play a critical role in mycobacterial cell wall biosynthesis and are considered as potential drug targets for the treatment of tuberculosis, especially multi-drug resistant forms of *M. tuberculosis*. Much of the research is now directed to the synthesis of natural products consisting of arabinofuranose rings as potential anti TB agents.

Article titled "Synthesis of octyl arabinofuranosides as substrates for mycobacterial arabinosyltransferases" by Jeongseok Han, Rajendrakumar Reddy et. al in Carbohydrate Research 338 (2003) 581-588, describes a panel of octyl oligosaccharides comprising of arabinofuranose rings. The process for glycosylation reactions involves coupling of octyl glycoside acceptors with the appropriate thioglycosides using N-iodosuccinimide and silver triflate activation. The synthesis disclosed provides substrates suitable for use in assays of mycobacterial arabinosyl transferases.

Article titled "Synthesis of deoxygenated all α(1→5)-linked arabinofuranose disaccharides as substrates and inhibitors of arabinosyltransferases of *Mycobacterium tuberculosis*" by Ashish K. Pathaka, Vibha Pathaka et al in Bioorganic & Medicinal Chemistry Volume 17, Issue 2, 15 Jan. 2009, Pages 872-881 discloses the synthesis and acceptor/inhibitory activity of Araf α(1→5) Araf disaccharides possessing deoxygenation at the reducing sugar of the disaccharide. Deoxygenation at either the C-2 or C-3 position of Araf was achieved via a free radical procedure using xanthate derivatives of the hydroxyl group (shown in figure below). The α(1→5)-linked disaccharides were produced by coupling n-octyl α-Araf 2-/3-deoxy, 2-fluoro glycosyl acceptors with an Araf thioglycosyl donor. The target disaccharides were tested in a cell free mycobacterial AraTs assay as well as an in vitro assay against MTB H37Ra and *M. avium* complex strains.

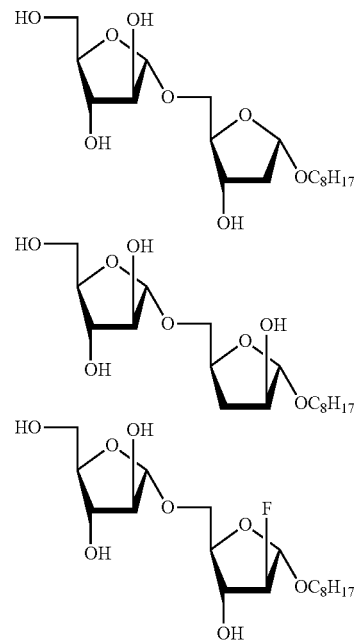

Article titled "Synthesis and Conformational Investigation of Methyl 4a-Carba-D-arabinofuranosides" by Christopher S. Callam and Todd L. Lowary J. Org. Chem. 2001, 66, 8961-8972 discloses the synthesis of carbasugar analogues of methyl α-D-arabinofuranoside and methyl β-D-arabinofuranoside (3 and 4) in identifying inhibitors of the arabinosyltransferases that are involved in the assembly of mycobacterial cell wall polysaccharides. Starting from D-mannose, the targets are obtained via a route in which the key steps are (i) a ring-closing metathesis and (ii) a subsequent stereoselective hydrogenation. The article further states that the route can also be applied to the preparation of other carbafuranoses through substitution of D-mannose with other pyranose sugars.

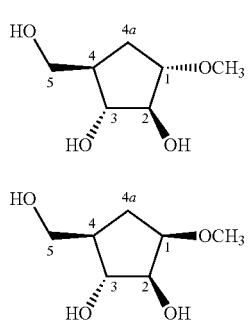

Article titled "Stereoselective synthesis of β-arabino glycosyl sulfones as potential inhibitors of mycobacterial Cell wall biosynthesis" by Benjamin Ayers, Hilary Long et. al in Carbohydrate Research Volume 344, Issue 6, 21 Apr. 2009, Pages 739-746, describes synthesis of a series of β-arabino glycosyl sulfones with varying alkyl chain lengths in a stereoselective fashion as putative mimics of decaprenol-phosphoarabinose (DPA), and as potential inhibitors of mycobacterial cell wall biosynthesis.

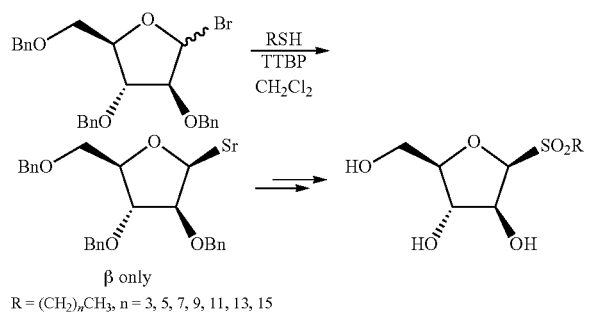

Article titled "Synthesis of methyl 5-S-alkyl-5-thio-d-arabinofuranosides and evaluation of their anti-mycobacterial activity" by Aditya K. Sankia, Julie Boucaua et al. in Bioorganic & Medicinal Chemistry, Volume 16, Issue 10, 15 May 2008, Pages 5672-5682, discloses synthesis of methyl 5-S-alkyl-5-thio-d-arabinofuranoside analogues as potential inhibitors of mycobacterial antigen 85 complex. The antigen 85 (ag85) complex which is a family of mycolyl transferases is involved in the synthesis of trehalose-6,6'-dimycolate and the mycolated hexasaccharide motif found at the terminus of the arabinogalactan in *mycobacterium*. Two of the compounds, 5-S-octyl-5-thio-α-D-arabinofuranoside (8) and 5-S-octyl-5-thio-β-d-arabinofuranoside (11) are disclosed to exhibit potential antibacterial activity against *Mycobacterium smegmatis* ATCC 14468.

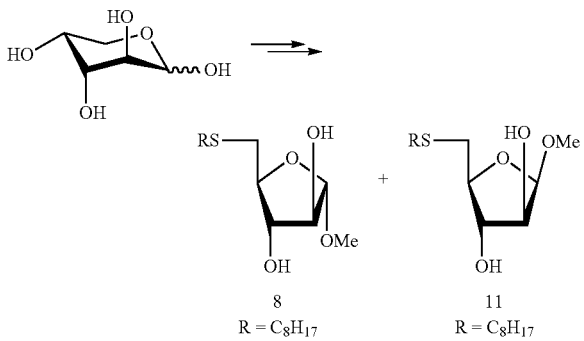

Further studies revealed that the enzyme arabinosyl transferases (AraT) involved in biosynthesis of AG and LAM utilize a single substrate i.e. β-decaprenyl-D-arabinofuranosyldiphosphate. This prompted a search for the mimics of the β-DPA as potential inhibitors for AraTs inter alia new anti-tubercular drug candidates.

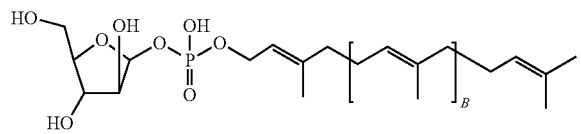

β-D-arabinofuranosyl-1-monophosphodecaprenol (β-DPA)

C. A. Centrone and T. L. Lowary, *J. Org. Chem.*, 2003, 68, 8115-8119; and in *J. Org. Chem.*, 2002, 67, 8862-8870; have reported the synthesis of various alkylated-C-phosphoryl-D-arabino-β-furanosides A and B as stable mimics of β-DPA and showed that the inhibitory activity of these compounds changes proportionally with the length of the alkyl chain. Related sulfone analogues C are observed to be weakly to modestly active. [C. A. Centrone and T. L. Lowary, Bioorg. Med. Chem., 2004, 12, 5495-5503]

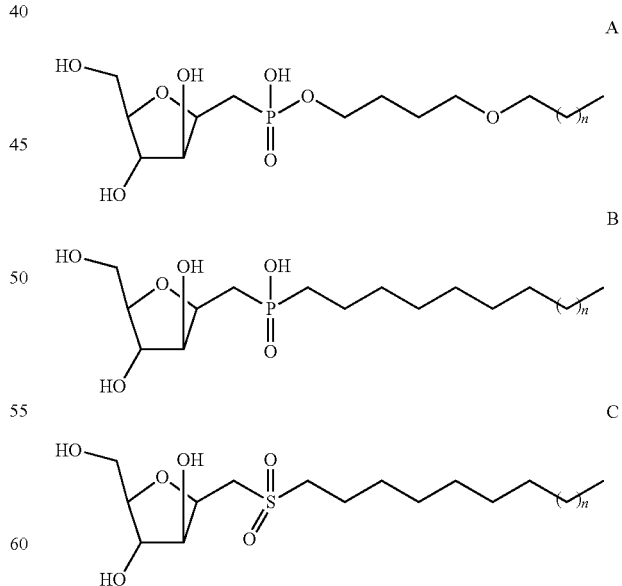

The present inventor in their earlier publication titled "Stereoselective Synthesis of β-C-Allyl- and β-C-Propargyl-D-arabinofuranosides" *Synthesis*, 2008, 1783-1787, have disclosed stereoselective synthesis of β-configured-C-allyl- and C-propargyl-D-arabinofuranosides (4,7-anhydro- 1,2,3-deoxy-D-gluco-oct-1-enitols and -oct-1-ynitols) by employing allylation/propargylation of a dialdofuranose under aqueous Barbier reaction conditions and acid-catalyzed furan ring transposition of 5-O-mesyl-manno-oct-7-eno- or 5-O-mesyl-manno-oct-7-ynofuranoside derivatives.

With a view that C-glycosides have the potential to serve as carbohydrate analogues resistant to metabolic processes, consequently, this class of compounds is currently receiving much interest as a potential source of therapeutic agents for clinical use. Some of these C-glycosides are found to be better than the frontline drug ethambutol and equal to other drugs available in the market for the treatment of tuberculosis. Moreover, they are non-toxic up to 100 µg/ml towards human cell lines.

The current inventors therefore felt a need to provide a new series of α and β-C-arabinofuranosides having long alkyl chains in general and with 10-undecenyl alkyl chain in particular (considering the easy availability of requisite coupling partners) and a terminal olefin for further fictionalizations as β-DPA mimics for the treatment of tuberculosis. Also, it is the subject of the invention to provide a stereoselective process which is simple, efficient for the synthesis of 10-undecenyl alpha and beta-C-arabinofuranosides employing a novel tetrahydrofuran ring transposition reaction and use of Grignard reagents for the key C—C bond forming reaction.

OBJECTS OF THE INVENTION

Main objective of the present invention is to provide 10-α/β-d-arabinofuranosyl-undecenes as potential anti-mycobacterial agents.

Another object of the present invention is to provide process for the preparation of 10-α/β-d-arabinofuranosyl-undecenes of general formula 1.

Yet another objective of the present invention is to provide pharmaceutical composition comprising compound of general formula II optionally along with pharmaceutically acceptable additives.

SUMMARY OF THE INVENTION

Accordingly, present invention provides a compound of general Formula (II)

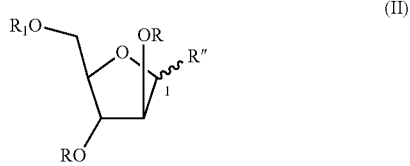

(II)

wherein, R" represents 10-undecenyl;
R1 represents hydrogen or α-D-Arabinofuranosyl or β-D-Arabinofuranosyl of Formula (A")

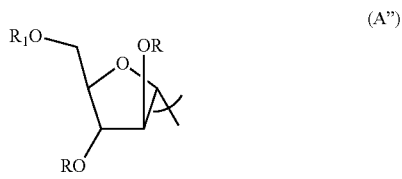

(A")

R in the general Formula (II) and in (A") is selected independently from hydrogen, acetyl, benzyl, alkoxy, methane sulfonyl, unsubstituted or substituted carboxyl, unsubstituted or substituted phenyl as given below:

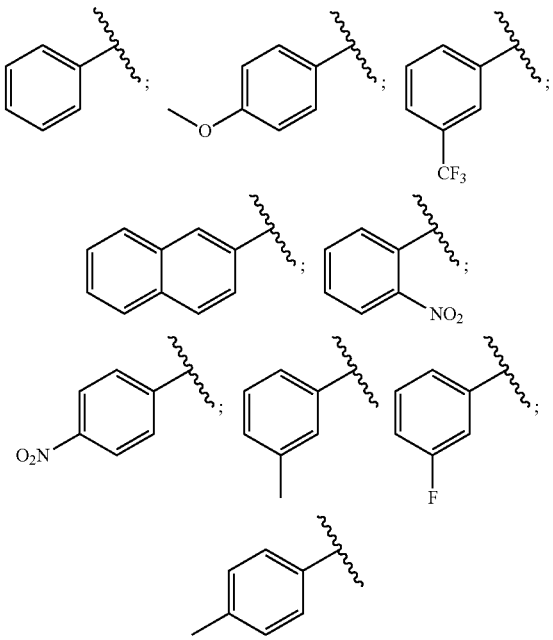

or unsubstituted or substituted alkyl, unsubstituted or substituted alkenyl, unsubstituted or substituted alkynyl, unsubstituted or substituted heterocycles.

In an embodiment; representative compounds of general formula (II) are:

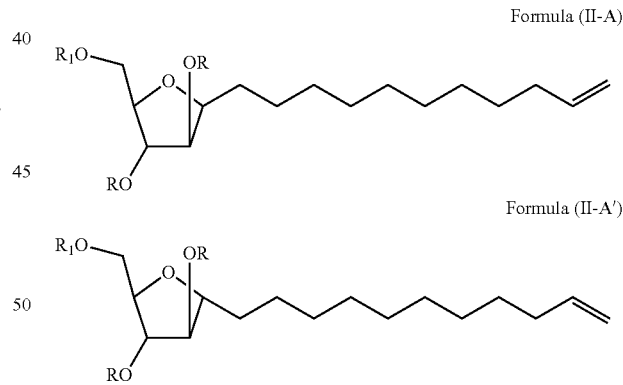

Formula (II-A)

Formula (II-A')

wherein C1 is in β configuration wherein C1 is in α configuration;
R and R1 are as defined in claim 1.

In yet another embodiment, representative compounds are;
10-β-D-Arabinofuranosylundecene (1);
10-α-D-Arabinofuranosylundecene (2);
α-D-Arabinofuranosyl-(1→5)-10-β-D-arabinofuranosylundecene (3);
α-D-arabinofuranosyl-(1→5)-10-α-D-arabinofuranosylundecene (4);
2,3-Di-O-benzyl-10-α-D-Arabinofuranosylundecene (16);

α-D-Arabinofuranosyl-(1→5)-2,3-Di-O-benzyl-10-α-D-Arabinofuranosylundecene (17);
2,3-Di-O-phenyl-10-α-D-Arabinofuranosylundecene (18);
2,3-Di-O-(4-methyoxy phenyl)-10-α-D-Arabinofuranosylundecene (19);
2,3-Di-O-(1-naphthyl)-10-α-D-Arabinofuranosylundecene (20);
2,3-Di-O-(3-nitrophenyl)-10-α-D-Arabinofuranosylundecene (21);
2,3-Di-O-(4-nitro phenyl)-10-α-D-Arabinofuranosylundecene (22);
2,3-Di-O-(3-methyl phenyl)-10-α-D-Arabinofuranosylundecene (23);
2,3-Di-O-(4-methyl phenyl)-10-α-D-Arabinofuranosylundecene (24);
2,3-Di-O-(3-flurophenyl)-10-α-D-Arabinofuranosylundecene (25);
2,3-Di-O-methyl-10-α-D-Arabinofuranosylundecene (26);
2,3-Di-O-octyl-10-α-D-Arabinofuranosylundecene (27);
10-α-D-Arabinofuranosylundecane (28);
2,3-Di-O-benzyl-10-β-D-Arabinofuranosylundecene (29);
2,3-Di-O-phenyl-10-β-D-Arabinofuranosylundecene (30);
2,3-Di-O-(4-methyoxy phenyl)-10-β-D-Arabinofuranosylundecene (31);
2,3-Di-O-(1-naphthyl)-10-β-D-Arabinofuranosylundecene (32);
2,3-Di-O-(3-nitrophenyl)-10-β-D-Arabinofuranosylundecene (33);
2,3-Di-O-(4-nitro phenyl)-10-β-D-Arabinofuranosylundecene (34);
2,3-Di-O-(3-methyl phenyl)-10-β-D-Arabinofuranosylundecene (35);
2,3-Di-O-(4-methyl phenyl)-10-β-D-Arabinofuranosylundecene (36);
2,3-Di-O-(3-flurophenyl)-10-β-D-Arabinofuranosylundecene (37);
2,3-Di-O-methyl-10-β-D-Arabinofuranosylundecene (38);
2,3-Di-O-octyl-10-β-D-Arabinofuranosylundecene (39);
10-β-D-Arabinofuranosylundecane (40).

In yet another embodiment of the present invention, said compounds are useful as anti mycobacterial agent in vitro.

In yet another embodiment, present invention provides a process for the preparation of compounds of formula (II) as claimed in claim 1 comprising the steps of:
(i) reacting an aldehyde (7) or an epoxide (12) with a grignard reagent in presence of copper catalyst and a solvent to obtain the alcohol (9) or (8) or mixture thereof;

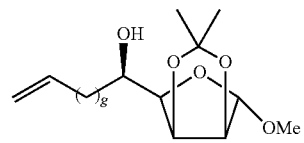

7

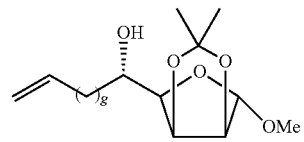

12

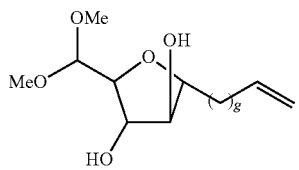

8

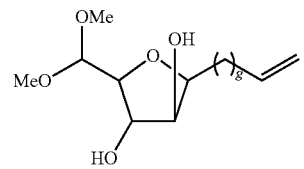

9

(ii) mesylating alcohol (9) or (8) as obtained in step (i) followed by acid mediated ring transposition to obtain acetals (11) or (5);

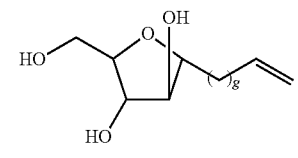

11

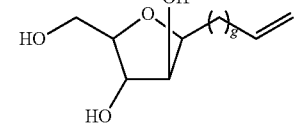

5

(iii) hydrolysing the acetals as obtained in step (ii) in presence of aqueous acid and subsequent reduction with alkali metal borohydride in lower alcohol of the intermediate aldehyde to obtain compound of formula (1) or (2);

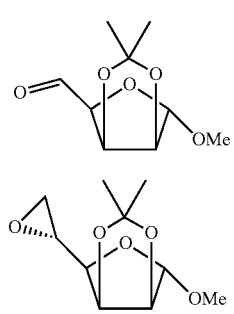

2

1

(iv) selective glycosylating at the C(5)-O— of compounds of formula (1) and (2) followed by debnzoylation to obtain dissachardes (3) and (4);

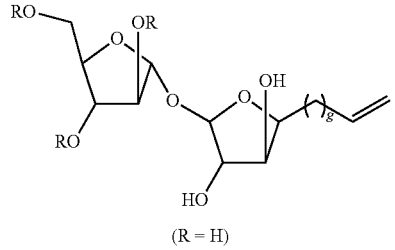

3

(R = H)

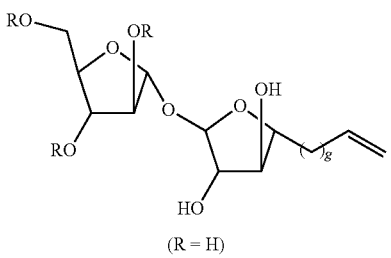

(R = H)

(v) alkylation or arylation of compounds of formula (5) and (11) or (3) and (4) followed by hydrolysis and subsequent reduction to obtain compounds of formula (II).

In yet another embodiment of the present invention, Grignard reagent used is selected from the group consisting of 9-decenyl-magnesium bromide or 10-undecenyl magnesium bromide.

In yet another embodiment of the present invention, the copper catalyst is selected from the group consisting of copper powder, Cu(II) halides, copper cyanide, copper triflate preferably copper cyanide.

In yet another embodiment of the present invention, the solvent used is selected from group consisting of diethyl ether, acetonitrile, THF or DMF.

In yet another embodiment of the present invention, the process for alkylation or arylation at C2 and C3 position of α-acetals (5) and (11) or disaccharides (3) and (4) comprising the steps of:

a. reacting acetals (5) and (11) or disaccharides (3) and (4) with corresponding alkyl halide R—X or aryl halide Ar—X in presence of sodium hydride or in presence of copper catalyst to obtain dialkyl or diaryl compounds;

wherein R is selected independently from unsubstituted or substituted alkyl, unsubstituted or substituted alkenyl, unsubstituted or substituted alkynyl, benzyl, unsubstituted or substituted phenyl

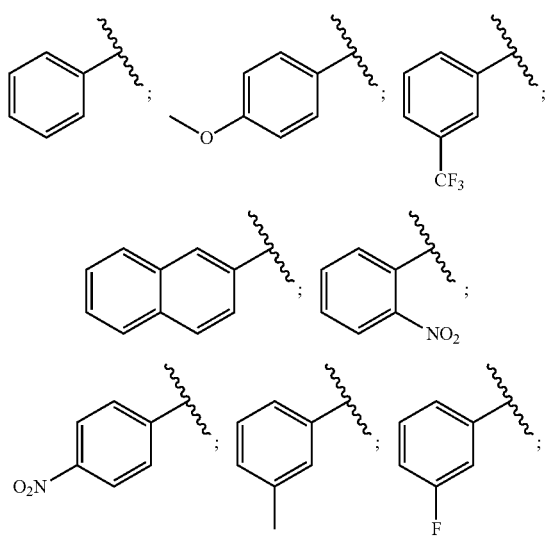

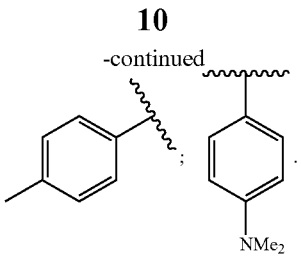

b. hydrolysing dialkyl or diaryl compounds using aq. Trifluoroacetic acid (TFA) and subsequent reduction with alkali metal borohydride in lower C1-C4 alcohol preferably isopropoanol to obtain alkylated or arylated compounds.

In yet another embodiment, present invention provides a pharmaceutical composition comprising the antimycobacterial compounds of Formula (II) in association with at least one pharmaceutically acceptable excipients.

In yet another embodiment, present invention provides method for treating tuberculosis in a subject, comprising administering an effective amount of the compounds of Formula (II) in association with pharmaceutical excipients.

In yet another embodiment, present invention provides use of the compounds of Formula (II) for preparation of medicament useful for treatment of tuberculosis.

In yet another embodiment, present invention provides a process for the preparation of compound of Formula 1 and the said process comprising the steps of:
(i) subjecting epoxide (12) to ring opening with 9-decenyl-magnesium bromide in presence of copper catalyst and a solvent to obtain alcohol (8);
(ii) mesylating of alcohol (8) followed by acid mediated ring transposition of the resulting mesylate (6) in lower alcohol to get dimethoxy acetal (5); and
(iii) hydrolysing the dimethoxy acetal (5) and subsequent reduction of the intermediate aldehyde to yield compound of Formula (1).

In yet another embodiment, present invention provides a process for the preparation of compound of Formula 2 and the said process comprising the steps of:
(i) reacting aldehyde (7) with 10-undecenyl magnesium bromide in presence of a solvent to get 1:4 epimeric mixture of alcohols (8) and (9) followed by separation of the major alcohol (9);
(ii) mesylating alcohol (9) foil owed by acid mediated ring transposition of the resulting mesylate (10) in lower alcohol to get dimethoxy acetal (11); and
(iii) hydrolysing the dimethoxy acetal (11) and subsequent reduction of the intermediate aldehyde to yield compound of Formula (2).

In yet another embodiment, present invention provides a process for the preparation of compound of Formula 3 and 4 and the said process comprising the steps of:
(i) selective glycosylation at the C(5)-O— of α/β-C-glycosides (1) and (2) by employing the Seeberger's arabinofuranosyl phosphate (13) as a glycosyl donor in the presence of catalytic TMSOTf to get the respective dissacheirdes (14) and (15); and
(ii) debenzoylation of (14) and (15) with alkoxide in lower alcohol to yield the disaccharides (3) and (4).

Figure 1B:
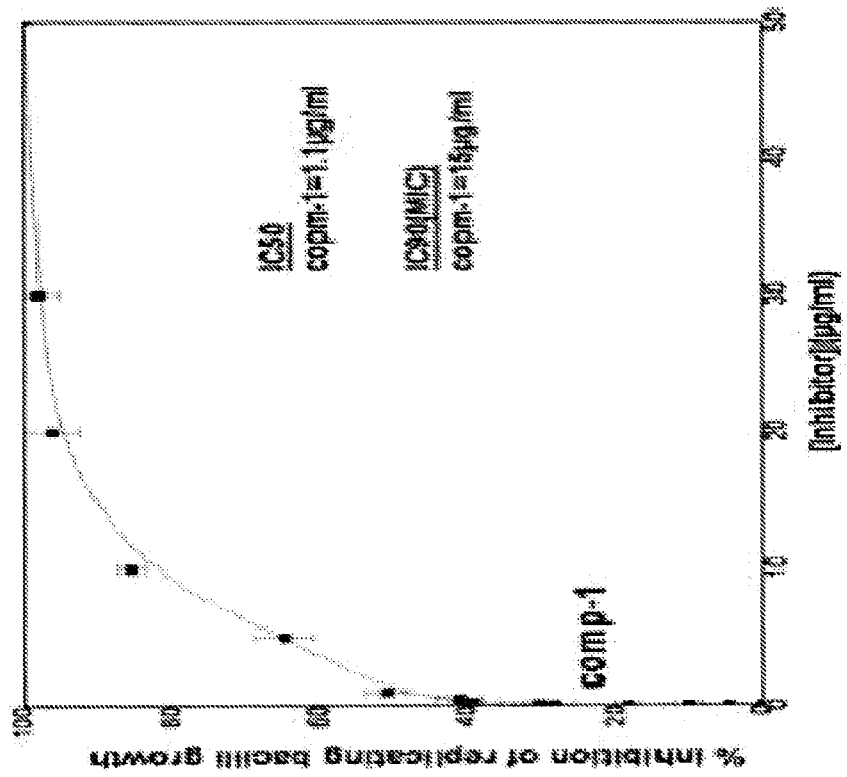
FIG. 1: Dose dependent effect of antimycobacterial inhibitors: a) ethambutol (■) and compound 2 (•), b) Compound 1 (■), c) Compound 3 (•) and 4 (■) d) Undecen-1-ol (■) e) rifampicin (■) against *M. bovis* BCG. Doses of all Compounds dissolved in DMSO ranging from 0.1 to 100 μg/ml were added at the time of inoculation and O.D was measured after 8 days of incubation at 620 nm. Experiments were carried out three times with duplicate cultures and results are mean±SD.

FIG. 2: Dose dependent effect of antimycobacterial inhibitors on mammalian cell lines: (a) Thp-1, (b) A431 and (c) HL-60. Doses of compounds dissolved in DMSO ranging from 1 to 10 μg/ml were added at the time of inoculation. Reduction of MTT dye indicating the % inhibition. Experiments were carried out three times with duplicate cultures and results are mean±SD.

FIG. 3: Dose dependent effect of antimycobacterial inhibitors: (A) 2,3-Di-O-benzyl-10-α-D-Arabinofuranosylundecene (B) α-D-Arabinofuranosyl-(1→5)-2,3-Di-O-benzyl-10-α-D-Arabinofuranosylundecene, *M. bovis* BCG. Doses of all Compounds dissolved in DMSO ranging from 0.1 to 100 μg/ml were added at the time of inoculation and O.D was measured after 8 days of incubation at 620 nm. Experiments were carried out three times with duplicate cultures and results are mean±SD

DETAILED DESCRIPTION OF THE INVENTION

The present invention relates to 10-α/β-D-Arabinofuranosylundecene (10-undecenyl α/β-C-arabinofuranosides) and to the process of synthesis thereof for inhibition of *M. bovis* BCG growth thus revealing them as potential candidates in the *Mycobacterium tuberculosis* drug development. All the known arabinofuranosyl transferases utilize a single substrate i.e. β-decaprenyl-D-arabino furanosyldiphosphate (I)

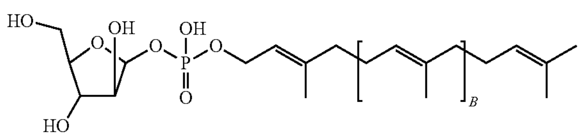

β-D-arabinofuranosyl-1-monophosphodecaprenol(β-DPA) (I)

In this regard, the present invention provides novel C-glycosides which entail methylene substitution for the anomeric oxygen offering a great deal of stability without substantial conformational amendment.

Present invention relates to 10-α/β-D-Arabinofuranosylundecene with anomeric carbon atom at C(1) of the general Formula (II) for inhibition of *M. bovis* BCG growth General formula (II)

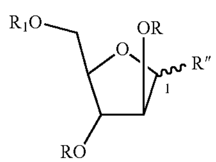

Wherein

R" represents 10-undecenyl;

R1 represents, hydrogen or α-D-Arabinofuranosyl or β-D-Arabinofuranosyl of Formula (A")

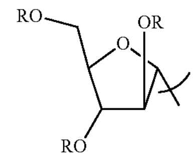

R in the general Formula (II) and in (A") is selected independently from hydrogen, acetyl, benzyl, alkoxy, methane sulfonyl, unsubstituted or substituted carboxyl, unsubstituted or substituted phenyl as given below:

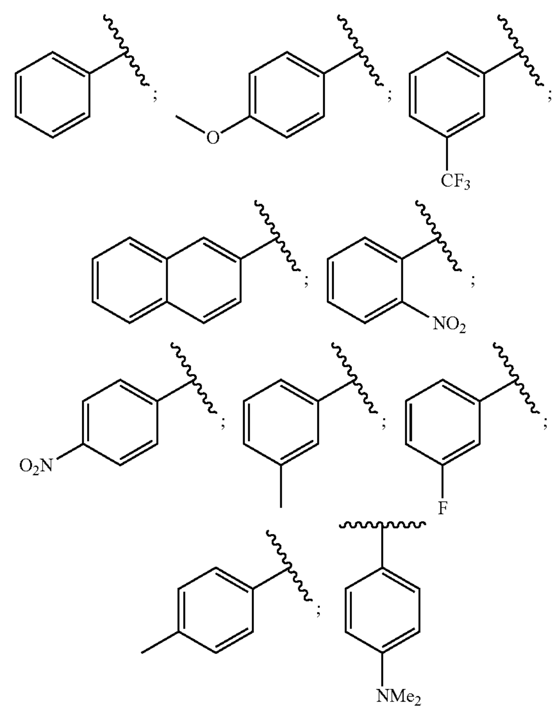

or unsubstituted or substituted alkyl, or unsubstituted or substituted alkenyl, or unsubstituted or substituted alkynyl, unsubstituted or substituted heterocycles.

The anomeric carbon at C(1) in compound of the general Formula (II) is represented as beta anomer of formula (II-A) and alpha anomer of formula (II-A') as below:

(II-A)

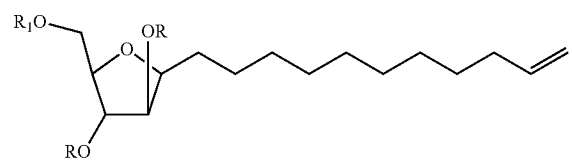

(II-A')

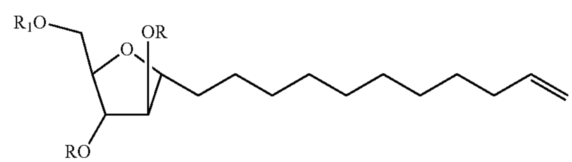

Wherein R1 and R in (II-A) and (II-A') are as described above.

Present invention discloses the compounds 1-4 to target enzymes involved in the biosynthesis of cell wall of *Mycobacterium* and thus useful as inhibitors against *Mycobacterium tuberculosis*.

Representative compounds of General formula (II) are:

Formula 1

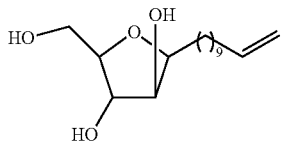

10-β-D-Arabinofuranosylundecene

C(1) is in β configuration (II-A),
R and R1 are hydrogen

Formula 3

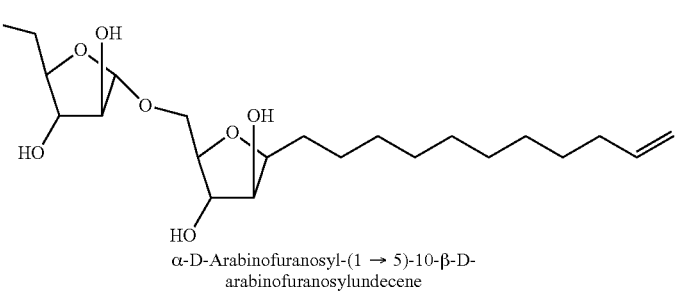

α-D-Arabinofuranosyl-(1 → 5)-10-β-D-arabinofuranosylundecene

C(1) is in β configuration (II-A),
R1 represents the group (A''),

; R is hydrogen

Formula 2

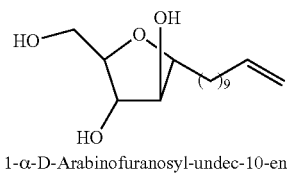

1-α-D-Arabinofuranosyl-undec-10-ene

C(1) is in α configuration (II-A'),
R and R1 are hydrogen

Formula 4

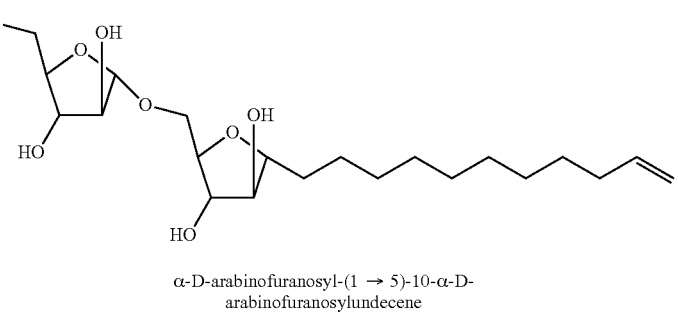

α-D-arabinofuranosyl-(1 → 5)-10-α-D-arabinofuranosylundecene

C(1) is in α configuration (II-A'),
R1 represents the group (A''),

; R is hydrogen

The compound of general formula (II) of the current invention encompasses the salts, enantiomers thereof.

General Process for the Preparation of Compound of Formula 1 and Formula 2

Present invention provides a simple, efficient process for the stereoselective synthesis of 10-α/β-D-Arabinofuranosylundecene with anomeric carbon atom at C(1), of the general Formula (2 or 1) comprises reacting an aldehyde (7) or an epoxide (12) with a grignard reagent under suitable reaction conditions to obtain the alcohol (9) or (8) followed by mesylation and acid mediated ring transposition to obtain acetals of formula (11) or (5). This is followed by hydrolysis and reduction to obtain the desired product (1) or (2). The relative stereochemistry obtained in the current process was observed to possess the 5R (6) and 5S (10) configuration.

1. General Process for the Preparation of Compound of Formula 2

The present invention provides a process for the preparation of α-C-arabinofuranosides (compound of Formula 2) comprising the steps of:

i. reacting aldehyde (7) with 10-undecenyl magnesium bromide in presence of diethyl ether to get 1:4 epimeric mixture of alcohols (8) and (9); separated the major alcohol (9);

ii. mesylating alcohol (9) followed by acid mediated ring transposition of the resulting mesylate (6) in lower alcohol to get dimethoxy acetal (11); and iii. hydrolysing the dimethoxy acetal (11) and reduction of the intermediate aldehyde to yield compound of Formula (2)

The process is given below in Scheme 1

Scheme 1

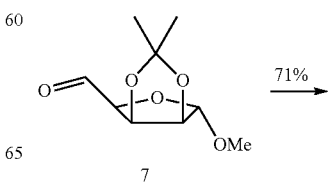

7

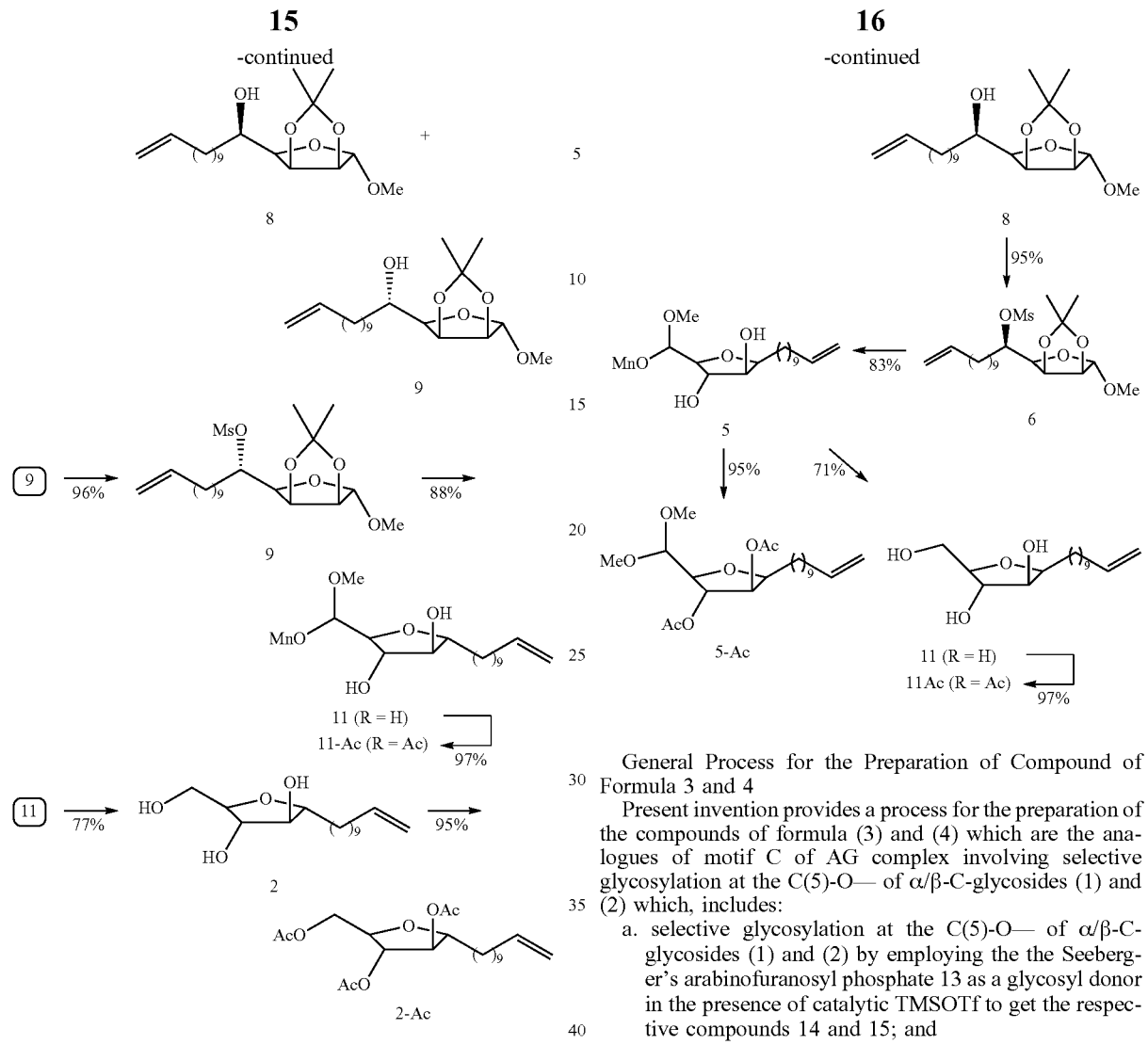

2. General Process for the Preparation of Compound of Formula 1

Present invention provides a process for the preparation of β-C-arabinofuranosides (compound of Formula 1) comprising:
i. subjecting epoxide (12) to ring opening with 9-decenyl magnesium bromide in presence of CuCN to obtain alcohol (8);
ii. mesylating alcohol (8) followed by acid mediated ring transposition of the resulting mesylate (6) in lower alcohol to get dimethoxy acetal (5); and
iii. hydrolysing the dimethyl acetal and reduction of the intermediate aldehyde to yield compound of Formula (1).

The process is given below in Scheme 2

General Process for the Preparation of Compound of Formula 3 and 4

Present invention provides a process for the preparation of the compounds of formula (3) and (4) which are the analogues of motif C of AG complex involving selective glycosylation at the C(5)-O— of α/β-C-glycosides (1) and (2) which, includes:
a. selective glycosylation at the C(5)-O— of α/β-C-glycosides (1) and (2) by employing the the Seeberger's arabinofuranosyl phosphate 13 as a glycosyl donor in the presence of catalytic TMSOTf to get the respective compounds 14 and 15; and
b. debenzoylation of 14 and 15 with alkoxide in lower alcohol to yield (3) and (4).

The process is given below in Scheme 3

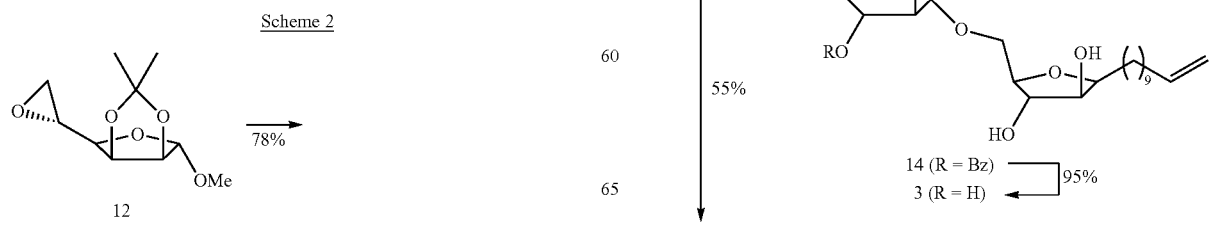

-continued

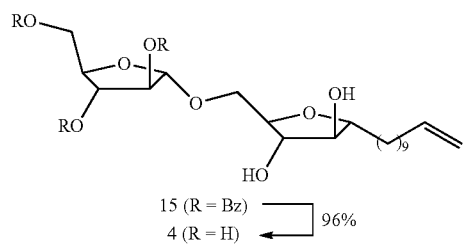

15 (R = Bz)
4 (R = H)
96%

General Process for the Alkylation or Arylation at C2 And C3 Position of A-Acetals (5) and (11) or Disaccharides (3) and (4)

Present invention provides alkylation or arylation at C2 and C3 position of acetal 5 and 11 and disaccharides 3 and 4 which exhibit potent inhibitory effect against *Mycobacterium Bovis* BCG.

The process of alkylation includes:

a. reacting acetals (5) and (11) with corresponding alkyl halide R—X or aryl halide Ar—X in presence of sodium hydride or in presence of copper catalyst to obtain dialkyl or diaryl compounds;

b. hydrolysing dialkyl or diaryl compounds using aq. TFA and subsequent reduction with alkali metal borohydride in lower C1-C4 alcohol; preferably isopropoanol.

Accordingly, the alkylation or arylation at C2 and C3 position of acetals 5 and 11 includes reacting α-C-Undec-11-enyl-D-Arabinofuranoside with the corresponding alkyl halide of the formula R—X in presence of copper catalyst and $Cs_2CO_3$ in a solvent to obtain diaryl compounds. The copper catalyst selected from copper powder, Cu(II) halide, copper cyanide, copper triflate, and the like.

The alkylation is effected in presence of sodium hydride as base in presence of polar aprotic solvents selected from diethyl ether, THF, DMF, DMSO and the like; preferably DMF and in presence of catalyst selected from $Bu_4NBr$.

| Sr. No. | R—X |
|---|---|
| 1 | MeI |
| 2 | 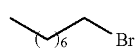  |
| 3 | 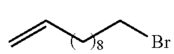  |
| 4 | 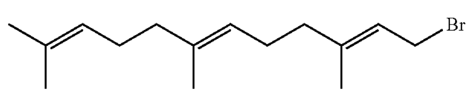  |
| 5 | 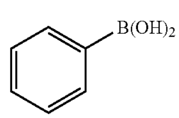  |
| 6 | 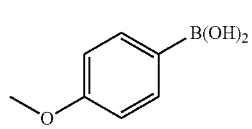  |

-continued

| | |
|---|---|
| 7 | 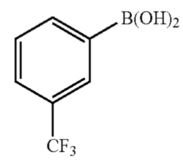  |

| Sr. No. | R |
|---|---|
| 8 | 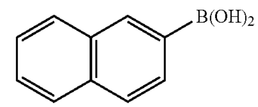  |
| 9 | 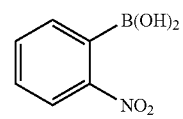  |
| 10 | 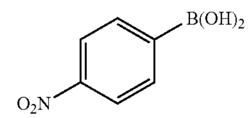  |
| 11 | 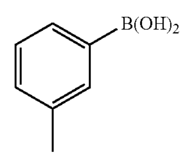  |
| 12 | 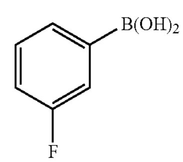  |
| 13 | 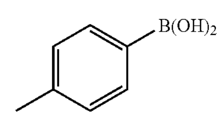  |
| 14 | 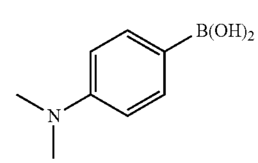  |

The alkylation or arylation is given in Scheme 4 to 6 below

Scheme 4
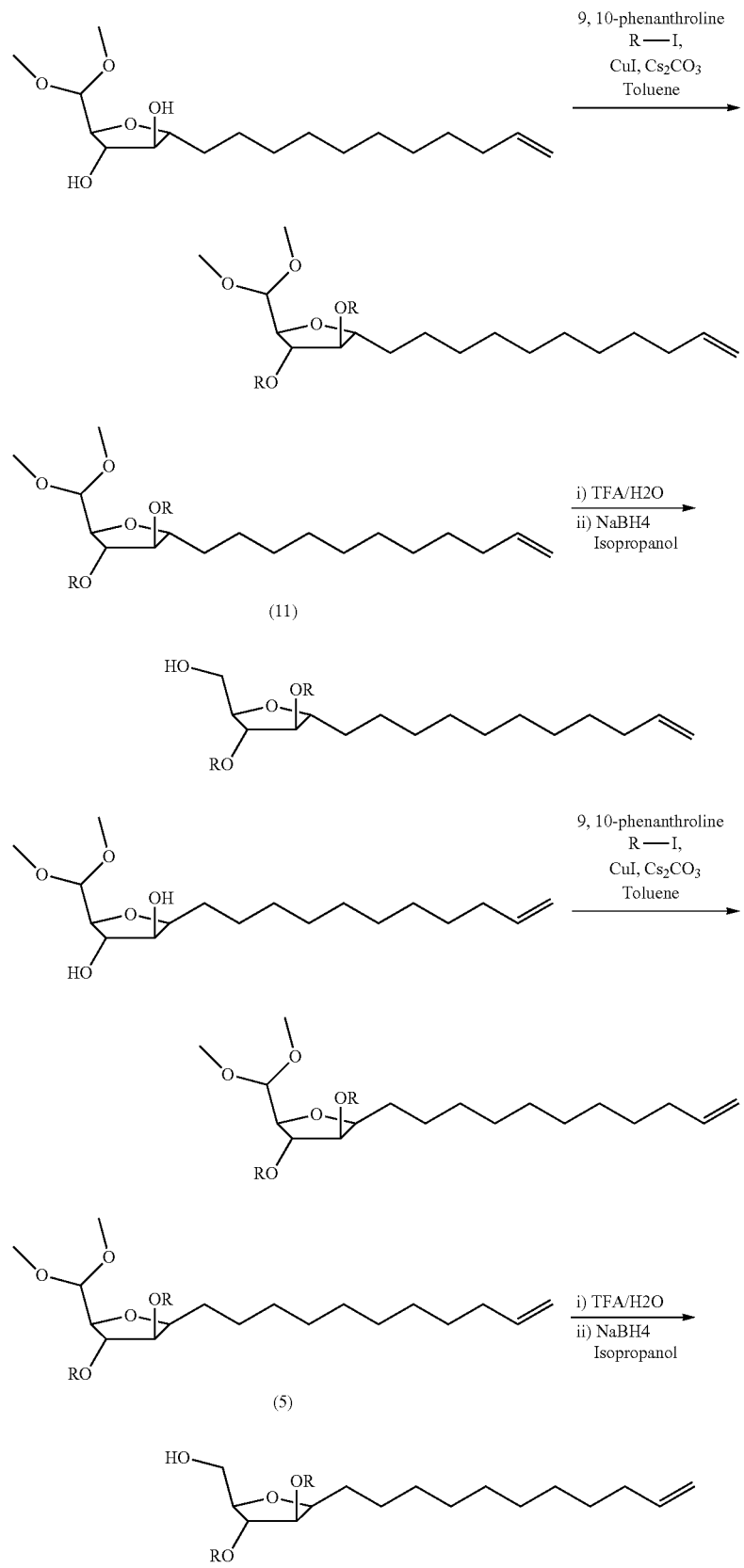

Scheme 5
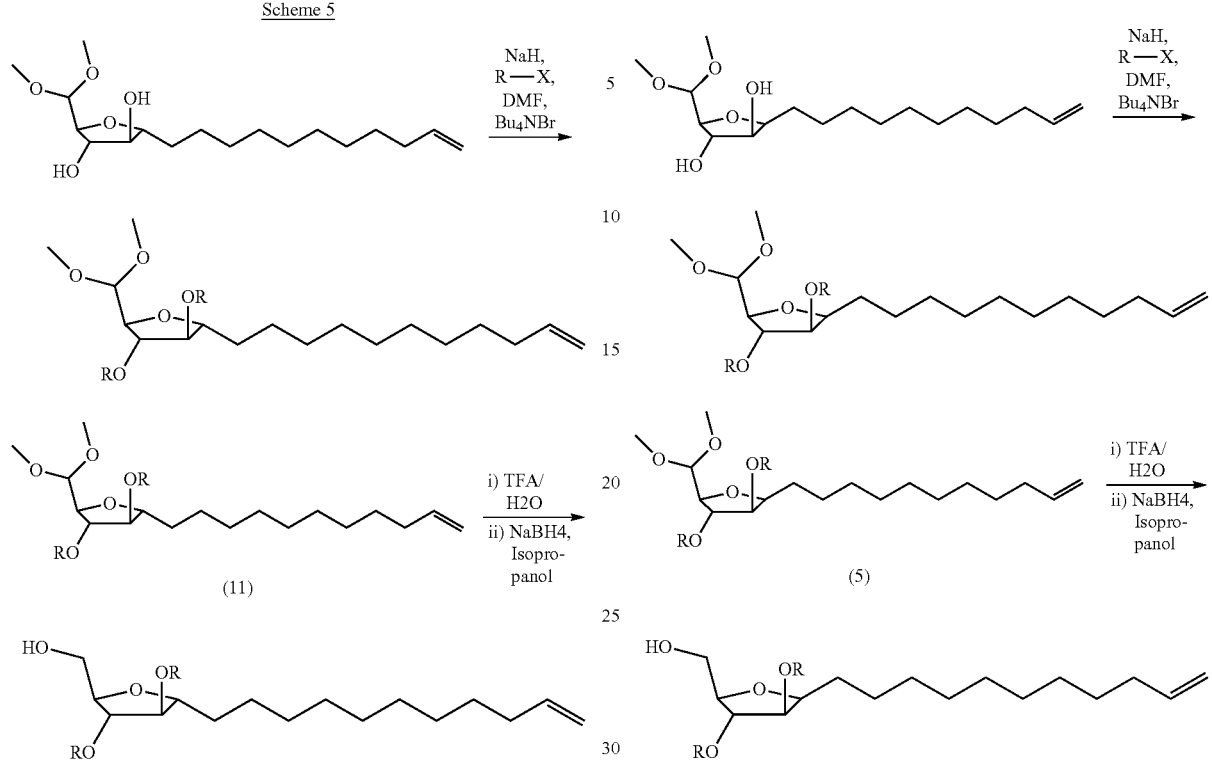
Scheme 6
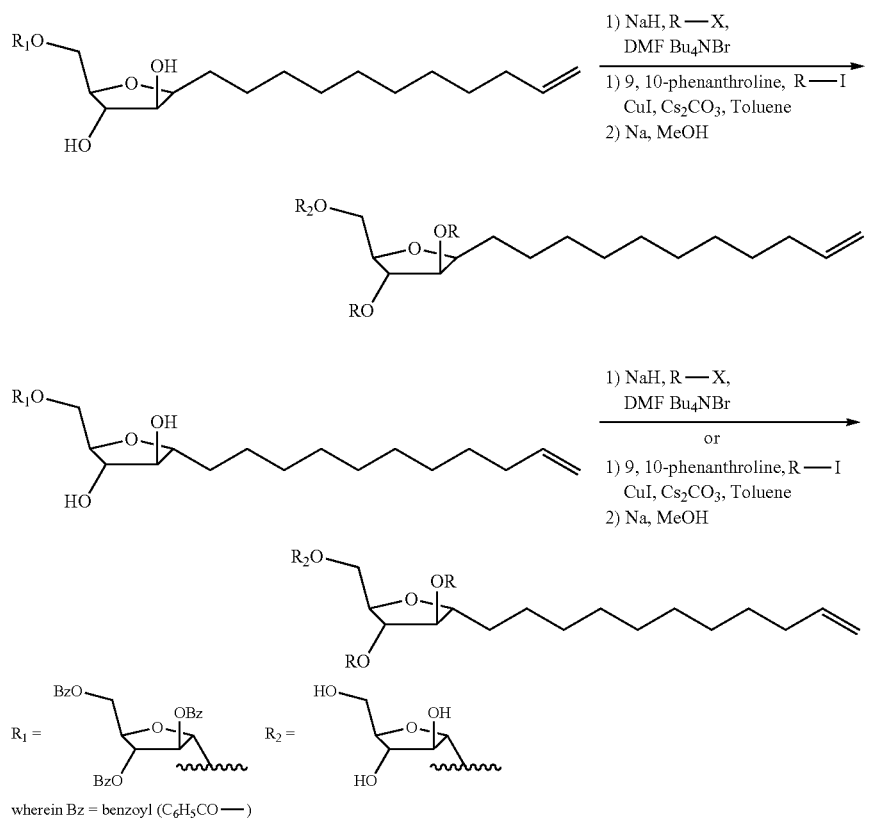
wherein Bz = benzoyl (C₆H₅CO—)

Anti-Mycobacterial Activity

Figure 1A:
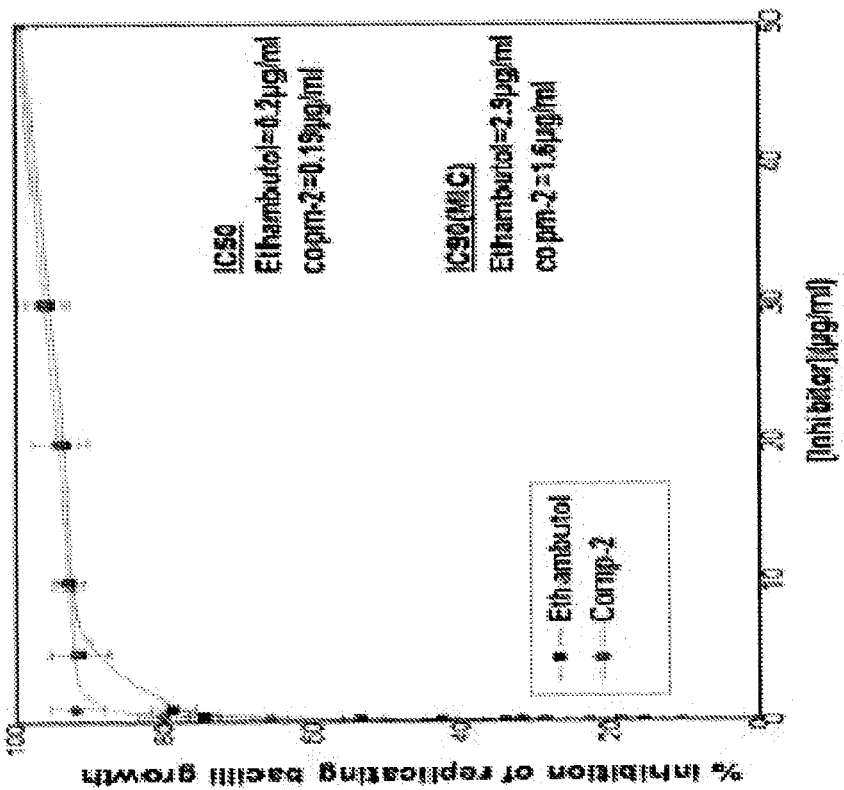
Figure 1C:
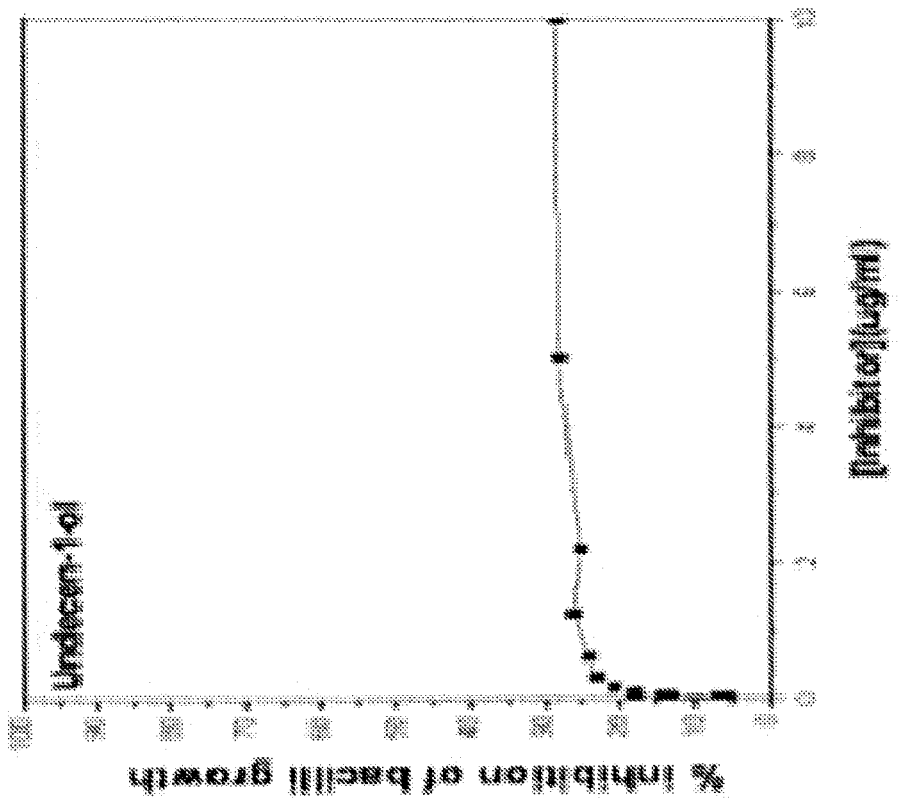
Figure 1D:
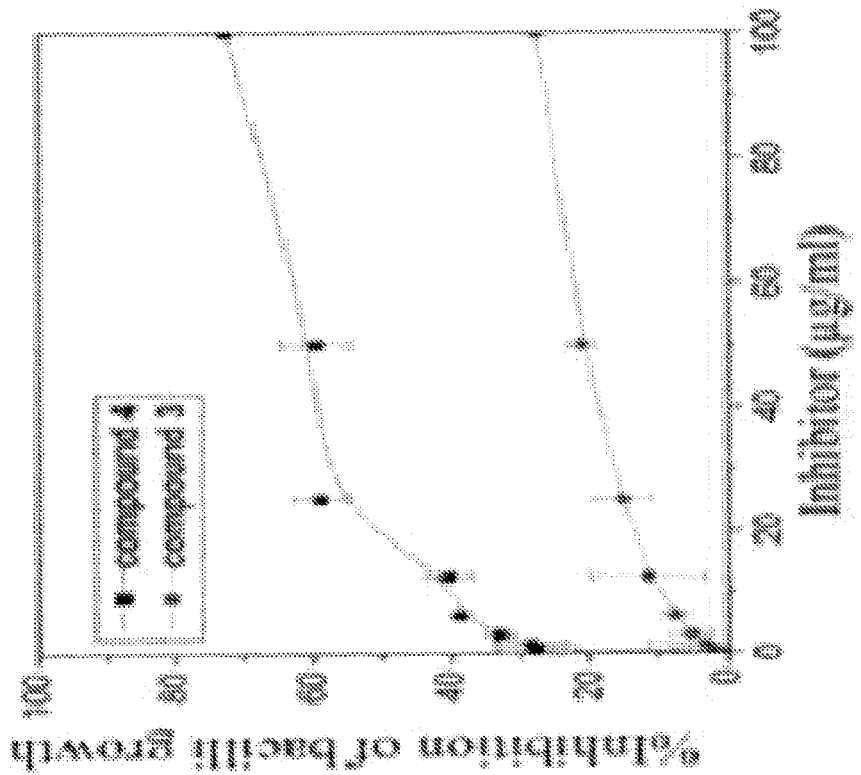
Figure 1E:
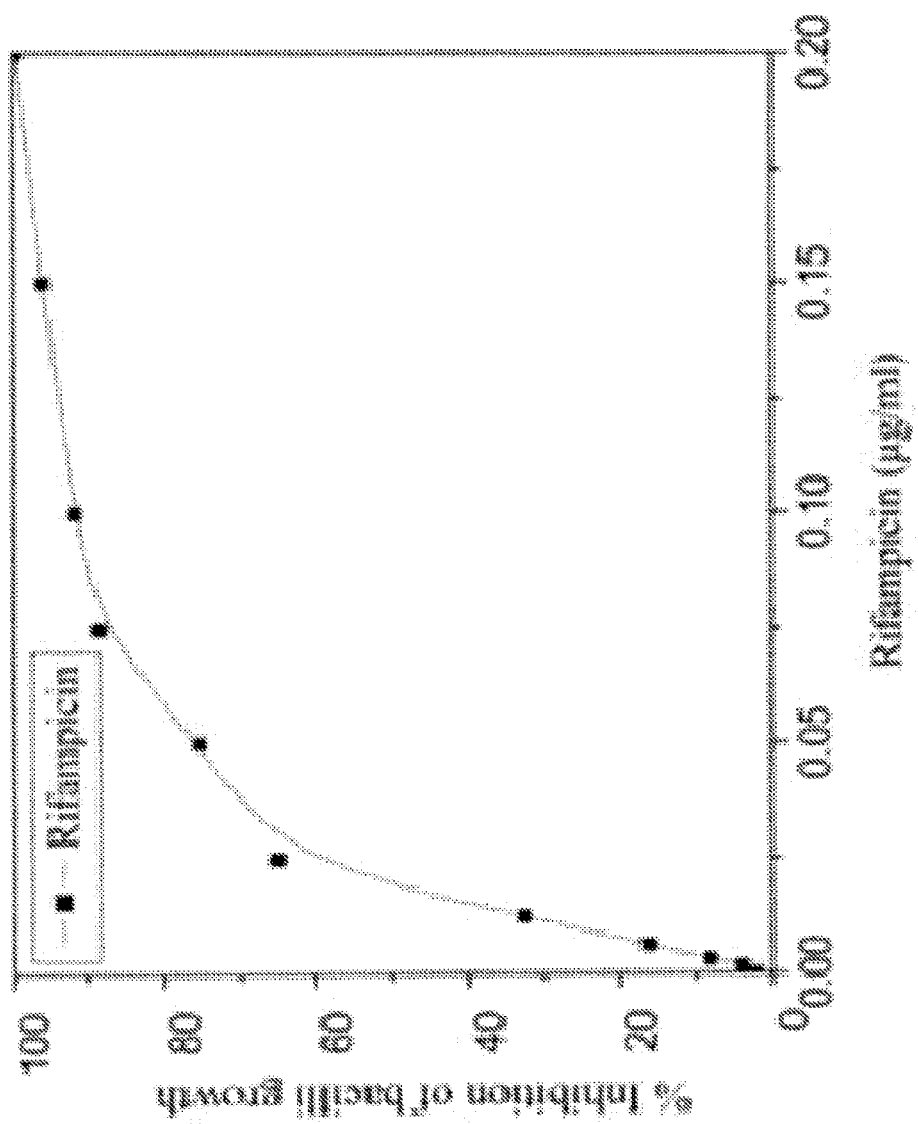

Present invention provides the anti-mycobacterial activity of the synthesized compounds 1-4. Accordingly, the *Mycobacterium bovis* BCG strain is used for the purpose and the inhibition studies are carried out on the whole cell based HTS assay employing rifampicin and ethambutol as controls. All the C-glycosides (except 3) displayed significant anti-mycobacterial effect at concentrations of 1 μg/mL (Table 1). The dose dependent inhibition of *M. bovis* BCG by compounds 1-4 [each at concentrations of 0 (control), 0.05, 0.1, 0.2, 0.3, 0.5 and 1 μg/mL] were carried out. As given in the table 1, compound 2 showed the best activity amongst the four tested with the IC50 (0.19 μg/ml), MIC (1.6 μg/ml, FIG. 1*a*) and its inhibition was comparable with that of the antitubercular drug, ethambutol, (FIG. 2*a*).

Surprisingly, the β-glycoside 1 (originally designed β-DPA mimic) is less active than 2 (FIG. 2*b*, FIG. 1*b*). Control experiments revealed that the corresponding aglycon 10-undecenol is a poor inhibitor (FIG. 1*d*) and thus rule out the possibility of a non-target related antimycobacterial activity of compounds 1-4. For obtaining the MICs the dose dependent inhibitions were carried out upto 50 μg for compounds 1, 2, and ethambutol and upto 100 μg for compounds 3 and 4.

TABLE 1

% of inhibition of growth of *Mycobacterium Bovis* BCG by compounds 1-4, Rifampicin and Ethambutol at 1 μg/ml concentration, and their IC50 & MIC values.

| Entry | Compound | % Inhibition | $IC_{50}$ (μg/ml) | $MIC_{90}$ (μg/ml) |
|---|---|---|---|---|
| 1 | 1 | 48 | 1.1 | 15 |
| 2 | 2 | 85 | 0.19 | 1.6 |
| 3 | 3 | <5 | >100 μg | — |
| 4 | 4 | 28 | 19 | — |
| 5 | Rifampicin | 99 (0.2 μg/ml) | 0.02 | — |
| 6 | Ethambutol | 85 | 0.2 | 2.9 |

Further, to evaluate the cytotoxicity of these compounds, the effect of compounds 1-4 on the metabolic function of the Thp-1, A431 and HL-60 human monocytic cells were examined using a standard MTT assay. No substantial growth inhibition of these cell lines is found up to 100 μg/ml concentration of these compounds (FIG. 2 given below) and thus these compounds do not have any significant cytotoxic effect on human cell lines.

From the data presented in Table 1, it is evident that the simple C-arabinofuranosides are more potent inhibitors than the corresponding disaccharides and their inhibitory activity is superior than the other C-analogues documented earlier. The superior inhibition of mono-C-arabinofuranosides over the disaccharides is quite remarkable and also important. Besra and co-workers have examined various O- and S-arabinofuranosides, the alkyl O-disaccharides and trisaccharides as acceptors for the arabinofuranosyl transferases and also as inhibitors of glycan synthesis. It has been revealed that the $C_8$-alkyl disaccharides are good substrates for the arabinofuranosyl transferases. The monosaccharides however turned out to be the poor substrates of the arabinofuranosyl transferases. The O-disaccharides showed inhibition with moderate MICs.

Moreover, the disaccharides with a α-anomeric configuration at the reducing end have better acceptor abilities inter alia the better inhibition when compared with the corresponding β-disaccharides. A similar trend is noticed with the α- and β-C-disaccharides 4 and 3 suggests that they might be acting as substrates for the arabinofuranosyl transferases. However, the superior inhibition of the monosaccharide 1 and 2 over corresponding disaccharides indicate that the mode of inhibition of 1 and 2 might be different from simply acting as acceptors.

The 2,3-di-methyl-α-C-undec-11-enyl-D-arabinofuranoside is shown to exhibit 91% inhibition at 20 ug/ml and all rest dialkylated or arylated derivative shown 0 to 45% inhibition at 20 ug/ml more potential inhibiting activity against *Mycobacterium bovis* BCG than the corresponding Motif C disaccharides.

The invention relates to a pharmaceutical composition comprising of the active ingredient of Formula (II), as defined above either alone or as its salts along with pharmaceutically acceptable excipients.

The pharmaceutical composition according to the invention can be in the form of a solid, for example, powders, granules, tablets, capsules or can be present in the liquid form such as solutions, emulsions, suspensions etc. or as an injectable composition.

The invention discloses the use of the potent compounds of formula II against *mycobacterium bacilli M. bovis* BCG.

The invention also provides methods for the treatment of the disorder discussed above. The α/β10-undecenyl C-arabinosides of Formula (II) and pharmaceutical compositions containing them may, according to the invention, be administered using any amount, any form of pharmaceutical composition and any route of administration effective for the treatment. After formulation with an appropriate pharmaceutically acceptable carrier in a desired dosage, as known by those of skill in the art, the pharmaceutical compositions of this invention can be administered by any means that delivers the active pharmaceutical ingredient (s) to the site of the body whereby it can exert a therapeutic effect on the patient.

EXAMPLES

Following examples are given by way of illustration therefore should not be construed to limit the scope of the invention.

General Methods: Air and/or moisture sensitive reactions were carried out in anhydrous solvents under an atmosphere of argon in oven-dried glassware. All anhydrous solvents were distilled prior to use: THF and diethyl ether from Na and benzophenone; MeOH, $CH_2Cl_2$ from $CaH_2$. Commercial reagents were used without purification. Column chromatography was carried out by using Spectrochem silica gel (60-120, 230-400 mesh). Optical rotations were determined on a Jasco DIP-370 digital polarimeter. Specific optical rotations [?]$_D$ are given in $10^{-1}$ degcm2g$^{-1}$. $^1H$ and $^{13}C$ NMR spectroscopy measurements were carried out on Bruker AC 200 MHz, or Bruker DRX 400 MHz or Bruker DRX 500 MHz spectrometers, and TMS was used as internal standard. $^1H$ and $^{13}C$ NMR chemical shifts are reported in ppm downfield from tetramethylsilane and coupling constants (J) are reported in hertz (Hz). The following abbreviations are used to designate signal multiplicity: s=singlet, d=doublet, t=triplet, q=quartet, m=multiplet, br=broad. Mass spectroscopy (ESI, API-QStar Pulsar) was carried out on a Finnigan MAT-1020 spectrometer. *M. bovis* BCG (ATCC35745) was obtained from AstraZeneca, India. The monocyte Thp-1 cell line was obtained from National Centre for Cell Science (NCCS), Pune, India.

Preparation and Characterization of the Compounds 1-4 and the Intermediates

Example 1: Methyl-6-deoxy-6-dec-16-ene-2,3-O-isopropylidene-α-L-Gulose (9)

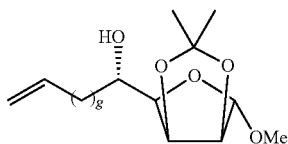

To a solution of aldehyde 7 (13.8 g, 68 mmol) in diethyl ether (150 mL) at −10° C. was added a solution of 10-undecenylmagnesium bromide [prepared from Mg (3.3 g, 136 mmol) and 11-bromo-undec-1-ene (27 mL, 123 mmol) in diethyl ether (150 mL) drop wise over 15 min]. The reaction mixture was warmed and allowed to stir at room temperature for 2 h, then it was treated with saturated NH4Cl solution (30 mL) and stirred at room temperature for 30 min. The organic phase was separated and the aqueous layer was extracted 3 times with 90 mL of ethyl acetate. The combined organic phase was washed with water, brine, dried over Na2SO4 and concentrated under reduced pressure. The crude product was purified by column chromatography (15:85 EtOAc:Hexane) to afford alcohol 9 (17.3 g, 71% yield) as colorless oil.

Rf=0.7 (25:75 EtOAc/pet ether); [α] D: +39.9 (c 1 CHCl3); $^1$H NMR (200 MHz, CDCl3): δ1.24-1.28 (br m, 17H), 1.45 (s, 3H), 1.51-1.60 (m, 2H), 1.96-2.06 (m, 2H), 2.88 (br s, 1H —OH), 3.31 (s, 3H), 3.75 (dd, J=3.7, 5.2 Hz, 1H), 3.99 (br dt, J=4.0, 6.0 Hz, 1H), 4.54 (d, J=6.0 Hz, 1H), 4.69 (dd, J=3.6, 6.0 Hz, 1H), 4.89 (ddt, J=1.2, 2.3, 10.1 Hz, 1H), 4.97 (ddt, J=1.6, 2.2, 17.0 Hz, 1H), 4.92 (s, 1H), 5.78 (ddt, J=6.7, 10.1, 17.1 Hz, 1H) ppm; $^{13}$C NMR (50 MHz, CDCl3): δ24.5 (q), 25.3 (t), 25.9 (q), 28.9 (t), 29.1. (t), 29.4 (t), 29.5 (t, 3C), 33.1 (t), 33.8 (t), 54.5 (q), 69.9 (d), 80.5 (d), 81.7 (d), 85.4 (d), 106.7 (d), 112.6 (s), 114.1 (t), 139.2 (d) ppm; ESI-MS: Anal. (C20H36O5) 379.30 ([M+Na]+, 100%), 395.39 ([M+K]+, 3%).

Example 2: Methyl 5-O-methanesulfonyl-6-deoxy-6-dec-16-ene-2,3-O-isopropylidene-α-L-Gulose (10)

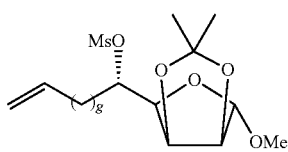

At 0° C., to a solution of alcohol 9 (4.5 g, 12.62 mmol) in anhydrous dichloromethane (60 mL) triethyl amine (5 mL, 38 mmol), mesyl chloride (1.2 mL, 15 mmol) was added slowly and the contents were stirred at the same temperature for 3 h. The reaction mixture was treated with ice water and partitioned between DCM and water. Organic layer was washed with aq. NaHCO3 solution, brine, dried over Na2SO4 and concentrated under reduced pressure. The crude product was purified by column chromatography (15:85 EtOAc:Hexane) to afford light yellow oil 10 (5.3 g, 96% yield).

Rf=0.7 (25:75 EtOAc:Hexane); [α]$_D$: +36.9 (c 1, CHCl3); $^1$H NMR (200 MHz, CDCl3): δ1.20-1.35 (br m, 17H), 1.44 (s, 3H), 1.63-1.81 (m, 2H), 1.96-2.06 (m, 2H), 3.10 (s, 3H), 3.28 (s, 3H), 3.98 (dd, J=3.4, 9.0 Hz, 1H), 4.55 (d, J=5.9 Hz, 1H), 4.64 (dd, J=3.5, 5.9 Hz, 1H), 4.85 (br dt, J=3.3, 9.0 Hz, 1H), 4.86-4.95 (m, 1H), 4.96 (ddt, J=1.6, 2.2, 17.2 Hz, 1H), 4.89 (s, 1H), 5.79 (ddt, J=6.7, 10.1, 17.2 Hz, 1H) ppm; $^{13}$C NMR (50 MHz, CDCl3): δ24.4 (t), 24.8 (q), 26.0 (q), 28.8 (t), 29.0 (t), 29.2 (t), 29.4 (t), 29.4 (t), 31.0 (t), 33.7 (t), 38.5 (q), 54.5 (q), 79.4 (d), 81.0 (d), 83.3 (d), 85.0 (d), 106.9 (d), 112.8 (s), 114.0 (t), 139.2 (d) ppm; ESI-MS: Anal. (C21H38O7) 457.41 ([M+Na]+, 15%), 379.44 (38%), 301.25 (38%), 304.30 (100%).

Example 3: 5-Deoxy-5-dimethylacetal-10-β-D-arabinofuranosylundecene (11)

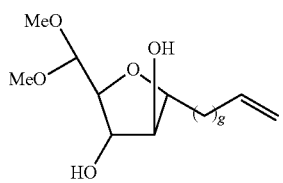

To a solution of mesylate 10 (4.3 g, 9.9 mmol) in anhydrous methanol (110 mL) was added p-TSA (340 mg, 1.98 mmol) and allowed to reflux at 80° C. for 72 h. After complete consumption of 10 as indicated by TLC, the reaction mixture was cooled and treated with solid NaHCO3 and stirred for 1 h. The contents were filtered through celite and concentrated under reduced pressure. The crude product was purified by column chromatography (30:70 EtOAc/Pet ether) to procure 11 (2.90 gm 88%). as a pale yellow color oil.

Rf=0.4 (50:50 EtOAc/Pet ether); [α]D: +20.0 (c 1, CHCl3); $^1$H NMR (200 MHz, CDCl3): δ1.20-1.40 (br m, 14H), 1.50-1.60 (m, 2H), 1.94-2.04 (m, 2H), 3.41 (s, 3H), 3.45 (s, 3H), 3.67 (br s, 1H —OH), 3.61-3.80 (br m, 2H), 3.83 (t, J=5.0 Hz, 1H), 3.97 (br s, 1H —OH), 4.14 (br t, J=4.4 Hz, 1H), 4.35 (d, J=4.8 Hz, 1H), 4.86 (ddt, J=1.2, 2.2, 10.1 Hz, 1H), 4.95 (ddt, J=1.5, 2.2, 17.1 Hz, 1H), 5.76 (ddt, J=6.7, 10.1, 17.1 Hz, 1H) ppm; $^{13}$C NMR (50 MHz, CDCl3): δ25.6 (t), 28.8 (t), 29.0 (t), 29.4 (t), 29.5 (t, 2C), 29.6 (t), 33.2 (t), 33.7 (t), 55.0 (q), 56.4 (q), 78.4 (d), 81.0 (d), 82.0 (d), 83.6 (d), 105.4 (d), 114.0 (t), 139.1 (d) ppm; ESI-MS: Anal. (C18H34O5) 353.26 ([M+Na]+, 100%), 301.27 (4%).

Example 4: 10-α-D-Arabinofuranosylundecene (2)

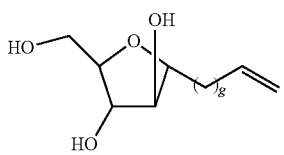

The dimethyl acetal 11 (350 mg, 1.06 mmol) was dissolved in 7 mL ice cold 70% aq. trifluoroacetic acid (TFA) and stirred at rt for 2 h. After complete consumption of the acetal 11 as indicated by TLC the reaction was concentrated under reduced pressure and the resulting crude (301 mg) was dissolved in isopropanol and treated with a solution of NaBH4 (120 mg, 3.18 mmol) in water (1.5 mL) and stirred at rt for 4 h. The reaction mixture was brought to acidic pH by adding 1N hydrochloric acid and extracted with diethyl ether (15×3 mL). The combined organic layer were washed with brine, dried over Na₂SO₄ and concentrated under reduced pressure. The crude product was purified by column chromatography (10:90 CH₃OH/CH₂Cl₂) to afford compound 2 (233 mg, 77% yield).

Rf=0.2 (10:90 CH₃OH/CH₂Cl₂) [α]$_D$: +29.77 (c 0.8, CHCl₃); ¹H NMR (400 MHz, CDCl₃): δ1.28-1.40 (br m, 14H), 1.56-1.63 (m, 2H), 2.02-2.06 (m, 2H), 3.61 (dd, J=5.3, 11.8 Hz, 2H), 3.69 (dd, J=3.5, 11.8 Hz, 1H), 3.71-3.74 (br m, 2H), 3.76 (dt, J=3.5, 5.3 Hz, 2H), 3.93 (t, J=5.5 Hz, 1H), 4.91 (ddt, J=1.1, 2.2, 10.2 Hz, 1H), 4.98 (br ddt, J=1.6, 2, 17.1 Hz, 1H), 5.80 (ddt, J=6.7, 10.2, 17.1 Hz., 1H) ppm; ¹³C NMR (100 MHz, CDCl₃): δ26.7 (t), 31.0 (t), 30.2 (t), 30.6 (t), 30.7 (t, 2C), 30.8 (t), 34.7 (t), 34.9 (t), 63.4 (t), 79.1 (d), 82.7 (d), 84.1 (d), 84.5 (d), 114.7 (t), 140.1 (d) ppm; ESI-MS: Anal. (C₁₆H₃₀O₄) 309.22 ([M+Na]⁺, 100%), 301.28 (22%).

Example 5: 5-Deoxy-5-dimethylacetal-2,3-di-O-acetyl-10-α-D-arabinofuranosylundecene (11Ac)

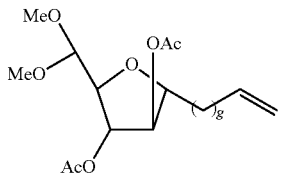

To an ice cooled solution of diol 11 (30 mg, 91 μmol) in pyridine (0.3 mL) acetic anhydride (0.2 mL) was added and reaction mixture was stirred for 2 h. The contents were poured in water and extracted with ethyl acetate. Combined organic layer was washed with sat. CuSO₄ solution, water followed by brine. The organic layer was dried over Na₂SO₄, concentrated under reduced pressure and the crude was purified by column chromatography (30:70 EtOAc/Pet ether) to afford 11 as a yellowish gum (36 mg, 97%).

Rf=0.3 (30:70 EtOAc/Pet ether). [α]D: +32.1 (c 1.3, CHCl3); IR (CHCl3) v: 3019, 2929, 2856, 1743, 1371, 1216, 1048, 757, 668; 1H NMR (400 MHz, CDCl3): δ1.20-1.30 (br m, 12H), 1.34-1.37 (m, 2H), 1.55-1.64 (m, 2H), 1.99-2.05 (m, 2H), 2.06 (s, 6H), 3.42 (s, 6H), 3.99 (dt, J=4.0, 6.0 Hz, 1H), 4.02 (dd, J=4.0, 6.0 Hz, 1H), 4.42 (d, J=6.1 Hz, 1H), 4.99 (dd, J=3.0, 4.0 Hz, 1H), 5.29 (dd, J=3.8, 2.8 Hz, 1H), 4.90 (ddt, J=1.2, 2.1, 10.2 Hz, 1H), 4.98 (br ddt, J=1.7, 2.0, 17.2 Hz, 1H), 5.79 (ddt, J=6.7, 10.2, 17.1 Hz, 1H); ¹³C NMR (100 MHz, CDCl3): δ20.9 (q, 2C), 25.4 (t), 28.9 (t), 29.1 (t), 29.4 (t, 2C), 29.5 (t), 29.7 (t), 32.4 (t), 33.8 (t), 53.9 (q), 55.3 (q), 78.6 (d), 81.2 (d, 2C), 83.2 (d), 103.4 (d), 114.1 (t), 139.2 (d), 169.8 (s), 170.1 (s); ESI-MS: Anal. (C22H38O7) 437.38 ([M+K]+, 100%), 455.35 (40.5%), 301.20 (38.5%), 485.40 (11.1%).

Example 6: Methyl 6-deoxy-6-dec-16-ene-2,3-O-isopropylidene-α-D-mannofuranoside (8)

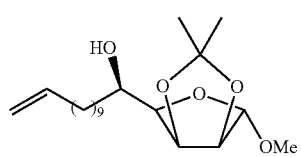

To a suspension of magnesium turnings (2.55 g, 104 mmol) in anhydrous diethyl ether (50 mL) was added 10-bromo-dec-1-ene (7.66 mL, 52 mmol) and the contents were heated to reflux for 2 h. The reaction mixture was diluted with diethyl ether (50 mL) and was transferred slowly to a stirring solution of anhydrous cuprous cyanide (7.52 g, 83 mmol) in diethyl ether (50 mL) at 0° C. then the contents stirred for additional 30 min at the same temperature. To this cooled dark brown colloidal suspension of the cuprate, was added a solution of the oxirane 12 (7.56 g, 35 mmol) in diethyl ether (50 mL) and stirred for 1 h at 0° C. and for 5 h at rt. Then the reaction mixture was quenched by adding cold water and extracted with ethyl acetate. Combined organic layer was washed with water, brine, dried over Na2SO4 and concentrated under reduced pressure. The crude product was purified by silica gel column chromatography (15:85 EtOAc:Hexane) to afford the compound 8 (9.7 g, 78% yield) as a low melting solid.

Rf=0.7 (25:75 EtOAc:Hexane). [α] D: +59.7 (c 1.0 CHCl3); ¹H NMR (200 MHz, CDCl3): δ1.23-1.30 (br m, 17H), 1.46 (s, 3H), 1.50-1.68 (m, 2H), 1.96-2.06 (m, 2H), 2.52 (d, J=5.7 Hz, 1H), 3.30 (s, 3H), 3.74 (dd, J=3.6, 7.3 Hz, 1H), 3.81-3.93 (m, 1H), 4.53 (d, J=6.0 Hz, 1H), 4.79 (dd, J=3.7, 6.0 Hz, 1H), 4.89 (br ddt, J=1.2, 2.2, 10.2 Hz, 1H), 4.90 (s, 1H), 4.98 (br ddt, J=1.6, 3.6, 16.0 Hz, 1H), 5.78 (ddt, J=6.7, 10.2, 17.2 Hz, 1H) ppm; ¹³C NMR (50 MHz, CDCl3): δ24.6 (q), 25.5 (t), 25.9 (q), 28.9 (t), 29.1 (t), 29.4 (t), 29.5 (t), 29.5 (t), 29.7 (t), 33.7 (t), 34.5 (t), 54.5 (q), 70.3 (d), 80.1 (d), 81.8 (d), 84.8 (d), 106.9 (d), 112.5 (s), 114.0 (t), 139.1 (d) ppm; ESI-MS: Anal. (C20H36O5) 304.28 (100%), 379.37 ([M+Na]+ 3%), 360.43 (4%).

Example 7: Methyl 5-O-methanesulfonyl-6-deoxy-6-dec-16-ene-2,3-O-isopropylidene-α-mannofuranoside (6)

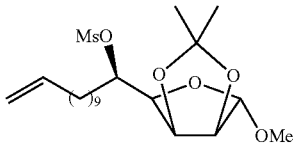

At 0° C., to a solution of alcohol 8 (8.8 g, 25 mmol) in anhydrous dichloromethane (150 mL) was added triethyl amine (8 mL, 61 mmol) and mesyl chloride (2.1 mL, 27 mmol) and stirred at same temperature for 3 h. Excess of mesyl chloride was quenched by adding ice. Usual work up followed by purification by column chromatography (15:85 EtOAc:Hexane) gave 6 (10.2 g, 95% yield) as light yellow oil.

Rf=0.7 (25:75 EtOAc:Hexane); [α] D: +12.8 (c 1, CHCl3); ¹H NMR (200 MHz, CDCl3): δ1.23-1.28 (br m, 17H), 1.45 (s, 3H), 1.70-1.93 (m, 2H), 1.96-2.00 (m, 2H), 3.06 (s, 3H), 3.30 (s, 3H), 3.98 (dd, J=3.4, 8.4 Hz, 1H), 4.55 (d, J=5.9 Hz, 1H), 4.69 (dd, J=3.5, 5.8 Hz, 1H), 4.86 (s, 1H), 4.87-4.93 (br m, 2H), 4.96 (br ddt, J=1.3, 2.0, 17.0 Hz, 1H), 5.78 (ddt, J=6.7, 10.2, 17.2 Hz, 1H) ppm; ¹³C NMR (50 MHz, CDCl3): δ23.6 (t), 24.9 (q), 26.0 (q), 28.9 (t), 29.1 (t), 29.3 (t), 29.4 (t, 2C), 29.6 (t), 32.2 (t), 33.8 (t), 38.3 (q), 54.7 (q), 78.5 (d), 79.0 (d), 80.2 (d), 84.8 (d), 107.0 (d), 112.8 (s), 114.0 (t), 139.2 (d) ppm; ESI-MS: (C21H38O7) 457.34 ([M+Na]+, 11%), 116.16 (100%), 301.34 (6%).

Example 8: 5-Deoxy-5-dimethylacetal-10-β-D-arabinofuranosylundecene (5)

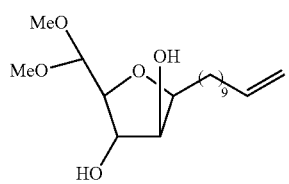

Following the procedure used for compound 11, the acid catalyzed rearrangement of the mesylate (4.0 g, 9.2 mmol) crude was purified by column chromatography (25:75 EtOAc/pet ether) to procure 5 (2.52 g, 83% yield) as light yellow color oil.

Rf=0.5 (50:50 EtOAc/pet ether); $[\alpha]_D$: +20.8 (c 1, CHCl$_3$); $^1$H NMR (200 MHz, CDCl$_3$): ⬚ ⬚ 1.24-1.37 (br m, 14H), 1.59-1.65 (m, 2H), 1.97-2.06 (m, 2H), 3.3 (br d, J=11.1 Hz, 1H), 3.48 (s, 3H), 3.54 (s, 3H), 3.74 (dd, J=2.6, 11.0 Hz, 1H), 3.82 (dd, J=1.7, 2.9 Hz, 1H), 3.92 (dt, J=2.7, 6.8 Hz, 1H) 4.25 (brs, 1H), 4.36 (d, J=3, 1H), 4.89 (ddt, J=1.3, 2.3, 10.1 Hz, 1H), 4.96 (ddt, J=1.5, 2.2, 17.1 Hz, 1H), 5.79 (ddt, J=6.7, 10.1, 17.2 Hz, 1H) ppm; $^{13}$C NMR (50 MHz, CDCl$_3$): δ26.1 (t), 28.2 (t), 28.9 (t), 29.1 (t), 29.5 (t, 3C), 29.7 (t), 33.7 (t), 56.4 (q), 57.8 (q), 77.1 (d), 77.9 (d), 82.1 (d), 85.7 (d), 105.2 (d), 114.1 (t), 139.2 (d) ppm; ESI-MS: Anal. (C$_{18}$H$_{34}$O$_5$) 301.27 ([M+1]$^+$, 100%), 353.35 ([M+Na]$^+$, 100%), 369.35 ([M+K]$^+$, 6%), 339.33 (30%), 301.28 (35%).

Example 9: 10-β-D-Arabinofuranosylundecene (1)

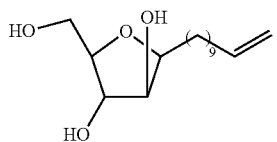

The dimethyl acetal 5 (500 mg, 1.5 mmol) was subjected for hydrolysis in 50% aq. trifluoro acetic acid (10 mL) followed by reduction with NaBH4 (171 mg, 4.5 mmol) according to the procedure used for 2, and the crude was purified by column chromatography (10:90 CH3OH/CH2Cl2) to acquire 1 (313 mg, 72% yield).

Rf=0.3 (10:90 CH3OH/CH2Cl2); [α]D: +25.9 (c 0.6, CHCl3). $^1$H NMR (400 MHz, CDCl3): δ1.31-1.44 (br s, 14H), 1.61-1.66 (m, 2H), 2.01-2.07 (m, 2H), 3.63 (dd, J=4.8, 11.5 Hz, 1H), 3.68 (dd, J=3.9, 11.5 Hz, 1H), 3.73 (ddd, J=2.5, 3.7, 4.6 Hz, 1H), 3.78 (br dd, J=0.9, 3.0 Hz, 1H), 3.91 (dt, J=3.1, 6.9 Hz, 1H), 3.96 (br dd, J=1.0, 2.4 Hz, 1H), 4.91 (ddt, J=1.2, 2.2, 10.1 Hz 1H), 4.98 (ddt, J=1.5, 2.2, 17.1 Hz 1H), 5.81 (ddt, J=6.8, 10.2, 17.1 Hz, 1H) ppm; $^{13}$C NMR (100 MHz, CDCl3): δ27.4 (t), 29.8 (t), 30.2 (t), 30.3 (t), 30.7 (t), 30.8 (t, 2C), 31.1 (t), 35.0 (t), 63.7 (t), 78.9 (d), 80.7 (d), 81.2 (d), 87.4 (d), 114.8 (t), 140.3 (d) ppm; ESI-MS: Anal. (C16H30O4) 2 87.40 ([M+1]+ 2%), 309.29 ([M+Na]+, 100%), 325.37 ([M+1<]+, 2%), 301.21 (11%).

Example 10: 5-Deoxy-5-dimethylacetal-2,3-di-O-acetyl-10-β-D-arabinofuranosylundecene (5Ac)

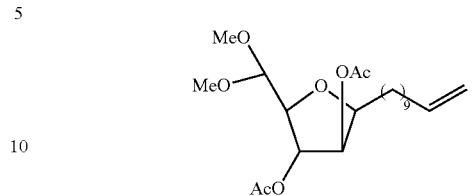

Following the procedure for synthesis of 11Ac, the diol 5 (25 mg, 76 μmol) was converted to the corresponding diacetate (30 mg, 95%).

Rf=0.4 (30:70 EtOAc/Pet ether). $[\alpha]_D$: +13.3 (c 2, CHCl$_3$); IR (CHCl$_3$) ⬚: 3019, 2928, 2855, 1743, 1372, 1215, 1088, 1047, 755, 668; $^1$H NMR (400 MHz, CDCl$_3$): δ1.20-1.30 (br m, 14H), 1.32-1.38 (m, 2H), 1.99-2.04 (m, 2H), 2.07 (s, 3H), 2.09 (s, 3H), 3.39 (s, 3H), 3.42 (s, 3H), 3.84 (dd, J=3.7, 6.4 Hz 1H), 3.94 (br dt, J=3.6, 6.0 Hz, 1H), 4.38 (d, J=6.4 Hz 1H), 4.90 (ddt, J=1.1, 2.0, 10.0 Hz, 1H), 4.96 (ddt, J=1.5, 2.6, 17.1 Hz, 1H), 5.13 (br d, J=3.5 Hz, 2H), 5.79 (ddt, J=6.7, 10.2, 17.1 Hz, 1H); $^{13}$C NMR (50 MHz, CDCl$_3$): δ20.7 (q), 20.9 (q), 25.9 (t), 28.3 (t), 28.9 (t), 29.1 (t), 29.39 (t), 29.4 (t, 2C), 29.6 (t), 33.8 (t), 53.8 (d), 55.1 (d), 77.3 (d), 78.9 (d), 81.0 (d), 82.2 (d), 103.6 (d), 114.1 (t), 139.2 (d), 169.4 (s), 169.6 (s); ESI-MS: Anal. (C$_{22}$H$_{38}$O$_7$) 437.32 ([M+Na]$^+$, 100%), 453.30 ([M+K]$^+$, 27.7%), 301.2 (38.5%), 432.36 (16.6%).

Example 11: 2,3,5-Tri-O-benzoyl-α-D-arabinofuranosyl-(1→5)-10-β-D-arabino furanosyl undecene (14)

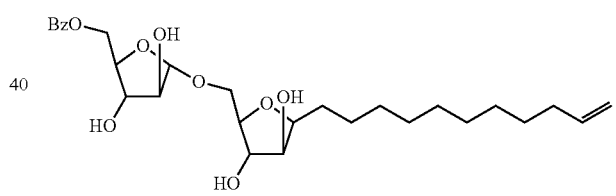

At 0° C., to a solution of orthoester (330 mg, 700 μmol) in anhydrous dichloromethane (5 mL) was added dibutyl phosphate (550 μl, 2.77 mmol) and stirred for 2 h at room temperature. The reaction mixture was treated with triethyl amine (2 mL) and concentrated under reduced pressure. The resulting crude product was purified on flash silica gel to get the phosphate 13 (344 mg, 73% yield) which was immediately subjected to next reaction.

At −33° C., in a solution of triol 1 (100 mg, 350 μmol) and phosphate 13 (344 mg, 523 μmol) in anhydrous dichloromethane was added TMSOTf (0.2 mL, 1.05 mmol) and stirred for 1 h at same temperature, to this triethylamine (3 mL) was added allowed to come at room temperature. The reaction mixture was concentrated under reduced pressure and purified by column chromatography (50:50 EtOAc/Pet ether) to procure the disaccharide (150 mg, 59% yield) as a colorless gum.

Rf=0.3 (50:50 EtOAc/Pet ether). $[\alpha]_D$: +1.7 (c 1, CHCl$_3$); $^1$H NMR (400 MHz, CDCl$_3$): δ1.24-1.31 (br s, 14H), 1.65-1.70 (m, 2H), 1.99-2.07 (m, 2H), 3.82 (br t, J=2.5 Hz, 1H), 3.87 (dd, J=2.9, 11.0 Hz, 1H), 3.88-3.89 (br m, 1H), 3.90 (dt, J=2.7, 6.8 Hz, 1H), 3.97 (dd, J=2.1, 11.0 Hz, 1H), 4.26 (d, J=2.2 Hz, 1H), 4.59 (ddd, J=3.3, 4.8, 5.3 Hz, 1H), 4.67 (dd, J=4.8, 11.9 Hz, 1H), 4.84 (dd, J=3.2, 11.9 Hz, 1H), 4.91 (br ddt, J=1.2, 2.0, 10.1 Hz, 1H), 4.98 (br ddt, J=1.7, 2.2, 17.0 Hz, 1H), 5.38 (s, 1H), 5.50 (d, J=1.2 Hz, 1H), 5.60 (dd, J=1.0, 5.2 Hz, 1H), 5.80 (ddt, J=6.7, 10.2, 17.0 Hz, 1H), 7.28 (t, J=7.9 Hz 2H), 7.38 (t, J=7.9 Hz, 2H), 7.44 (t, J=7.9 Hz, 2H), 7.49 (t, J=1.3, 7.5 Hz, 1H), 7.56-7.59 (m, 2H), 7.98 (dd, J=1.3, 7.9 Hz, 2H), 8.02 (dd, J=1.3, 7.9 Hz, 2H), 8.13 (dd, J=1.3, 7.9 Hz, 2H) ppm; $^{13}$C NMR (100 MHz, CDCl$_3$): δ26.2 (t), 28.1 (t), 28.9 (t), 29.4 (t), 29.5 (t), 29.8 (t), 29.7 (t), 29.8 (t), 33.8 (t), 63.6 (t), 67.4 (t), 77.6 (d), 78.5 (d), 79.7 (d), 81.4 (d), 82.0 (d), 82.2 (d), 84.3 (d), 106.4 (d), 114.1 (t), 128.3 (d, 2C), 128.4 (d, 2C), 128.5 (d, 2C), 128.7 (s), 128.8 (s), 129.6 (s), 129.7 (d, 2C), 129.9 (d, 2C), 130.1 (d, 2C), 133.1 (d), 133.6 (d), 133.63 (d), 139.2 (d), 165.5 (s), 165.9 (s), 166.2 (s) ppm; MALDI-TOF: Anal (C$_{42}$H$_{50}$O$_{11}$) 445.21 (100%), 533.32 (48%), 753.25 ([M+Na]$^+$, 38%), 769.20 ([M+K]$^+$, 10%).

Example 12: α-D-Arabinofuranosyl-(1→5)-10-β-D-arabinofuranosylundecene (3)

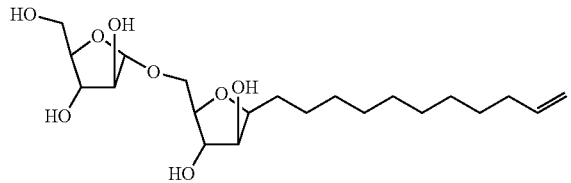 [SMILES: C=CCCCCCCCCCC1OC(COC2OC(CO)C(O)C2O)C(O)C1O]

The tribenzoate 14 (50 mg, 68 μmol) was taken in methanol (5 mL) and a catalytic Na was added. After 2 h stirring at room temperature, the reaction mixture was concentrated and purified by column chromatography (10:90 CH2Cl2/CH3OH) to procure the free disaccharide (27 mg, 95% yield).

Rf=0.2 (10:90 CH2Cl2/CH3OH); [α]D: +61.7 (c 1, CH3OH); $^1$H NMR (400 MHz, CDCl3): δ1.29-136 (br m, 14H), 1.61-1.66 (m, 2H), 2.02-2.07 (m, 2H), 3.59 (dd, J=4, 9.7 Hz, 1H), 3.63 (dd, J=5.4, 11.9 Hz, 1H), 3.73 (dd, J=3.4, 11.9 Hz, 1H), 3.79-3.85 (m, 5H), 3.89 (dt, J=3.4, 7.0 Hz, 1H), 3.96-3.97 (br m, 2H) 3.98 (d, J=1.1 Hz, 1H), 4.90 (ddt, J=1.2, 2.1, 10.1 Hz, 1H), 4.93 (d, J=1.2 Hz, 1H), 4.97 (ddt, J=1.7, 2.1, 17.0 Hz, 1H) 5.81 (ddt, J=6.7, 10.2, 17.1 Hz, 1H) ppm; $^{13}$C NMR (100 MHz, CDCl3): δ27.3 (t), 29.7 (t), 30.2 (t), 30.3 (t), 30.7 (t), 30.8 (t), 30.9 (t), 31.0 (t), 35.0 (t), 63.2 (t), 69.1 (t), 78.8 (d), 79.2 (d), 80.9 (d), 83.2 (d), 83.3 (d), 85.6 (d), 86.1 (d), 109.7 (d), 114.8 (t), 140.3 (d) ppm; MALDI-TOF: Anal (C21H38O8) 441.21 ([M+Na]+, 100%), 457.21 ([M+K]+, 39%).

Example 13: 2,3,5-Tri-O-benzoyl-α-D-arabinofuranosyl-(1→5)-10-α-D-arabino furanosyl undecene (15)

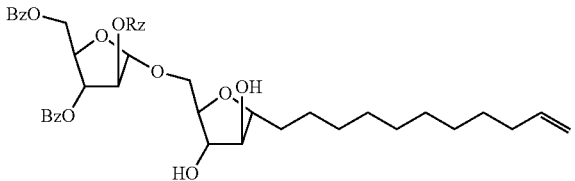

The glycosidation of the compound 2 (115 mg, 401 μmol) was carried out as outlined in the preparation of 14 employing freshly prepared phosphonate (394 mg, 602 μmol), the crude was purified by column chromatography (50:50 EtOAc/Pet ether) to get the tribenzoyl disaccharide Rf=0.2 (50:50 EtOAc/Pet ether); [α]D: +7.6 (c 0.5, CHCl3); $^1$H NMR (400 MHz, CDCl3): δ1.22-1.38 (br m, 14H), 1.58-1.61 (m, 2H), 2.0-2.04 (m, 2H,), 3.2 (br s, 2H —OH), 3.77 (dd, J=4.0, 10.8 Hz, 1H), 3.84 (dd, J=6.3, 12.5 Hz, 1H), 3.86 (t, J=5.2 Hz, 1H), 3.95 (dd, J=3.8, 10.9 Hz, 1H), 3.98 (dd, J=4.0, 5.7 Hz, 1H), 4.24 (t, J=5.2 Hz, 1H), 4.61 (dt, J=3.5, 4.8 Hz, 1H), 4.65 (dd, J=4.8, 11.8 Hz, 1H), 4.81 (dd, J=3.3, 11.8 Hz, 1H), 4.92 (ddt, J=1.2, 2.0, 10.2 Hz, 1H), 4.98 (ddt, J=1.7, 2.0, 17.1 Hz, 1H), 5.38 (s, 1H), 5.53 (d, J=1.4, 1H), 5.59 (dd, J=1.4, 5.1 Hz, 1H), 5.80 (ddt, J=6.7, 10.2, 17.1 Hz, 1H), 7.28 (t, J=7.8 Hz, 2H), 7.37 (t, J=7.8 Hz, 2H), 7.43 (t, J=7.8 Hz, 2H), 7.49 (t, J=1.2, 7.2 Hz, 1H), 7.54-7.58 (m, 2H), 7.97 (dd, J=1.2, 8.1 Hz, 2H), 8.02 (dd, J=1.2, 8.1 Hz, 2H), 8.13 (dd, J=1.2, 8.2 Hz, 2H) ppm; $^{13}$C NMR (100 MHz, CDCl3): δ25.6 (t), 28.9 (t), 29.1 (t), 29.4 (t), 29.5 (t, 2C), 29.6 (t), 33.3 (t), 33.8 (t), 63.6 (t), 67.6 (t), 77.6 (d), 79.5, (d), 80.9 (d), 81.0 (d), 82.0 (d), 82.3 (d), 83.5 (d), 106.2 (d), 114.1 (t), 128.3 (d, 2C), 128.5 (d, 4C), 128.7 (s), 128.8 (s), 129.5 (s), 129.7 (d, 2C), 129.9 (d, 2C), 130.0 (d, 2C), 133.1 (d, 2C), 133.5 (d), 133.6 (d), 139.2 (d), 165.7 (s), 165.8 (s), 166.3 (s) ppm; MALDI-TOF: Anal (C42H50O11) 445.05 (100%), 518.38 (54%), 533.16 (46%), 753.11 ([M+Na]+, 47%), 769.03 ([M+K]+, 18%). (161 mg, 55% yield) as a colourless gum.

Example 14: α-D-arabinofuranosyl-(1→5)-10-α-D-arabinofuranosylundecene (4)

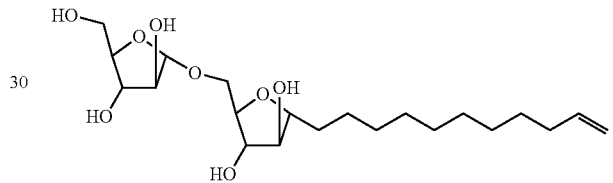

To a solution of tribenzoate 15 (40 mg, 54 μmol) in methanol (5 mL) catalytic amount of Na was added and stirred for 2 h. The reaction mixture was concentrated and purified by column, chromatography (10:90 CH2Cl2/CH3OH) to obtain 4 (22 mg, 96% yield).

Rf=0.2 (10:90 CH2Cl2/CH3OH); [α]D: +31.1 (c 0.4, CH3OH); 1H NMR (400 MHz, CDCl3): δ1.29-137 (br m, 14H), 1.56-1.63 (m, 2H), 2.02-2.07 (m, 2H), 3.59 (dd, J=3.6, 10.7 Hz, 1H), 3.62 (d, J=5.2 Hz, 1H), 3.65 (d, J=5.4 Hz, 1H), 3.71-3.74 (m, 2H), 3.75 (t, J=3.3 Hz 1H), 3.82 (dd, J=5.3, 11 Hz, 1H), 3.83 (dd, J=3.0, 6.0 Hz, 1H), 3.87 (dt, J=3.8, 5.3 Hz, 1H), 3.97 (dd, J=3.3, 5.7 Hz, 1H), 3.98-4.02 (br m, 2H), 4.92 (ddt, J=1.1, 2.0, 10.1 Hz, 1H), 4.93 (d, J=1.3 Hz, 1H), 4.97 (ddt, J=1.6, 2.0, 17.2 Hz, 1H), 5.80 (ddt, J=6.7, 10.2, 17.0 Hz, 1H) ppm; $^{13}$C NMR (100 MHz, CDCl3): δ26.7 (t), 30.1 (t), 30.2 (t), 30.6 (t), 30.7 (t, 2C), 30.8 (t), 34.6 (t), 34.9 (t), 63.1 (t), 68.7 (t), 78.9 (d), 79.6 (d), 82.8 (d), 82.9 (d), 83.2 (d), 84.3 (d), 85.9 (d), 109.6 (d), 114.7 (t), 140.2 (d) ppm; MALDI-TOF: Anal (C21H38O8) 441.10 ([M+Na]+, 100%), 533.15 (71%), 551.15 (54%), 628.48 (55%).

Example 15: 2,3,5-Tri-O-acetyl-10-β-D-Arabinofuranosylundecene (1-Ac)

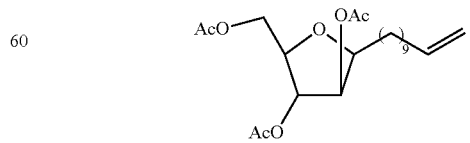

Following the procedure for synthesis of 11Ac, the triol 1 (42 mg, 146 μmol) was converted to the corresponding triacetate (58 mg, 97%).

Rf=0.7 (25:75 EtOAc/Petether); [α]$_D$: +6.4 (c 3.4, CHCl$_3$). $^1$H NMR (400 MHz, CDCl$_3$): δ1.24 (bs, 14H), 1.48-1.63 (m, 2H), 1.95-2.04 (m, 2H), 2.06 (s, 6H), 2.09 (s, 3H), 3.98-402 (m, 2H), 4.12 (dd, J=6.5, 11.5 Hz, 1H), 4.33 (dd, J=4.7, 11.5 Hz, 1H), 4.86-4.91 (m, 1H), 4.95 (ddt, J=1.7, 2.2, 17.2 Hz, 1H), 5.16 (dd, J=0.83, 3.5 Hz, 1H), 5.77 (ddt, J=6.8, 10.1, 17.2 Hz, 1H) ppm; $^{13}$C NMR (100 MHz, CDCl$_3$): δ 20.68 (q), 20.74 (q), 20.79 (q), 25.92 (t), 28.24 (t), 28.83 (t), 29.03 (t), 29.32 (t), 29.36 (t), 29.38 (t), 29.49 (t), 33.72 (t), 63.90 (t), 76.99 (d), 79.01 (d), 80.92 (d), 80.99 (d), 114.05 (t), 139.13 (d), 169.64 (s), 169.71 (s), 170.71 (s); ESI-MS: Anal. (C$_{22}$H$_{36}$O$_7$) 413.14 ([M+1]$^+$, 4%), 435.19 ([M+Na]$^+$, 100%), 451.15 ([M+K]$^+$, 3%).

Example 16: 2,3,5-Triacetyl-10-α-D-Arabinofuranosylundecene (2-Ac)

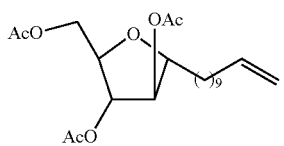

Following the procedure for synthesis of 11Ac, the triol 2 (35 mg, 122 μmol) was converted to the corresponding triacetate (47 mg, 95%).

Rf=0.6 (20:80 EtOAc/Petether) [α]$_D$: +16.50 (c 0.761, CHCl$_3$). $^1$H NMR (400 MHz, CDCl$_3$): δ 1.26 (bs, 14H), 1.34-1.38 (m, 2H), 1.59-1.63 (m, 2H), 2.08 (s, 6H), 2.09 (s, 3H), 4.0 (ddd, J=3.8, 7.0, 13.7 Hz 1H), 4.14 (ddd, J=3.9, 5.0, 8.7 Hz 1H), 4.22 (dd, J=6.0, 11.6 Hz 1H), 4.26 (dd, J=5, 11.6 Hz 1H), 4.91 (ddt, J=1.2, 2.4, 10.3 Hz 1H), 4.97 (ddt, J=1.1, 2.1, 17.1 Hz 1H), 5.06 (dd, J=2.4, 3.7 Hz 1H), 5.80 (ddt, J=6.7, 10.2, 17.3. Hz, 1H) ppm; $^{13}$C NMR (100 MHz, CDCl$_3$): δ 20.80 (q), 20.82 (q), 20.90 (q), 25.46 (t), 28.92 (t), 29.10 (t), 29.39 (t), 29.44 (t), 29.46 (t, 2C), 32.43 (t), 33.78 (t), 63.46 (t), 78.92 (d), 80.21 (d), 80.95 (d), 83.15 (d), 114.10 (t), 139.21 (d), 170.02 (s), 170.05 (s), 170.72 (s); ESI-MS: Anal. (C$_{22}$H$_{36}$O$_7$) 413.14 ([M+1]$^+$, ~1%), 435.31 ([M+Na]$^+$, 100%).

Example 17: 2,3-Di-O-benzyl-10-α-D-Arabinoturanosylundecene (16)

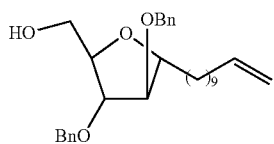

$^1$H NMR (400 MHz, CDCl$_3$): δ 1.20-1.40 (br m, 14H), 1.56-1.64 (m, 2H), 1.99-2.08 (m, 2H), 2.16 (br s, 1H, —OH), 3.68-3.70 (m, 2H), 3.82 (dd, J=0.7, 2.6 Hz, 1H), 3.96-4.04 (br m, 2H), 4.09 (dd, J=4.3, 9.2 Hz, 1H), 4.53 (s, 2H), 4.55 (s, 2H), 4.88-5.06 (br m, 2H), 5.85 (ddt, J=6.6, 10.3, 17.03 Hz, 1H), 7.26-7.40 (br m, 10H); $^{13}$C NMR (100 MHz, CDCl$_3$): 25.6 (t), 28.8 (t), 29.0 (t), 29.4 (t, 3C), 32.9 (t), 33.7 (t, 2C), 62.6 (t), 71.5 (t), 71.9 (t), 82.6 (d), 82.7 (d), 84.4 (d), 87.2 (d), 114.0 (t), 127.6 (d), 127.6 (d, 2C), 127.7 (d), 128.3 (t, 2C), 128.3 (t, 2C), 137.5 (s), 137.6 (s), 139.0 (s); ESI-MS: Anal. (C$_{30}$H$_{42}$O$_4$) 505.65 ([M+K]$^+$, 100%), 489.68 (40.5%).

Example 18: α-D-Arabinofuranosyl-(1→5)-2,3-Di-O-benzyl-10-α-D-Arabino furanosyl undecene (17)

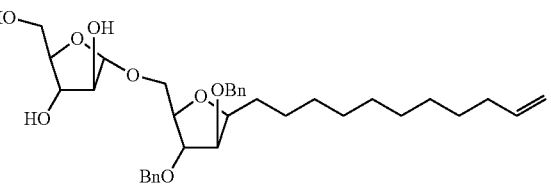

$^1$H NMR (400 MHz, CDCl$_3$): δ1.20-1.40 (br m, 14H), 1.55-1.64 (m, 2H), 2.00-2.05 (m, 2H), 2.87 (s, 1H), 2.95 (s, 1H), 3.56 (dd, J=3.8, 10.3 Hz, 1H), 3.70-3.80 (m, 2H), 3.83 (dd, J=6.2, 10 Hz, 1H), 3.86 (dd, J=1.8, 3.6 Hz, 1H), 3.95 (br s, 1H), 3.97 (br m, 1H), 3.99 (br s, 1H), 4.02 (br s, 1H), 4.12 (ddd, J=3.8, 5.9, 9.4 Hz, 1H), 4.40-4.57 (m, 4H), 5.0 (s, 1H), 4.89-5.02 (br m, 2H), 5.80 (ddt, J=6.6, 10.3, 16.9 Hz, 1H), 7.26-7.38 (br m, 10H); $^{13}$C NMR (100 MHz, CDCl$_3$): 28.9 (t), 29.1 (t), 29.3 (t), 29.5 (t), 29.7 (t, 3C), 31.9 (t), 33.8 (t), 62.0 (t), 62.6 (t), 71.7 (t), 71.8 (t), 77.2 (d), 78.0 (d), 78.9 (d), 81.1 (d), 83.0 (d), 85.4 (d), 87.1 (d), 87.3 (d), 107.6 (d), 114.1 (t), 127.7 (d), 128.0 (d, 2C), 128.5 (d), 129.7 (d), 137.5 (s), 139.2 (s), 7.27-7.38 (br m, 10H) ppm; ESI-MS: Anal. (C$_{35}$H$_{50}$O$_8$): 621.78 [M+Na]$^+$

Example 19: 2,3-Di-O-phenyl-10-α-D-Arabinofuranosylundecene (18)

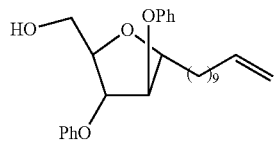

[α]$_D^{26}$: +1.6 (c 1.1, CHCl$_3$); $^1$H NMR (400 MHz, CDCl$_3$): δ 1.20-1.40 (br m, 16H), 1.99-2.10 (m, 2H), 2.17 (br s, 1H, —OH), 3.80-3.91 (m, 2H), 4.23 (ddd, J=1.8, 5.4, 11.0 Hz, 1H), 4.30 (ddd, J=4.1, 7.5, 12.1 Hz, 1H), 4.65 (br m, 1H), 4.85 (d, J=3.2 Hz, 1H), 4.93 (ddd, J=1.2, 3.5, 10.2 Hz, 1H), 4.93 (ddd, J=1.6, 3.5, 16.5 Hz, 1H), 5.85 (ddt, J=6.6, 10.2, 16.5 Hz, 1H), 6.65-7.05 (m, 6H), 7.22-7.33 (m, 4H); $^{13}$C NMR (100 MHz, CDCl$_3$): 25.7 (t), 28.9 (t), 29.1 (t), 29.4 (t), 29.5 (t, 3C), 32.2 (t), 33.8 (t), 62.3 (t), 82.4 (d), 82.8 (d), 82.3 (d), 85.6 (d), 114.1 (t), 115.7 (d, 2C), 115.8 (d, 2C), 121.7 (d, 2C), 129.7 (d, 4C), 139.2 (d), 157.0 (s), 157.1 (s) ppm; ESI-MS: Anal. (C$_{28}$H$_{38}$O$_4$) 461.59 [M+Na]$^+$.

Example 20: 2,3-Di-O-(4-methyoxy phenyl)-10-α-D-Arabinofuranosylundecene (19)

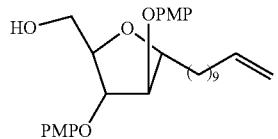

[α]$_D$: +29.7.1 (c 2.3, CHCl$_3$); $^1$H NMR (400 MHz, CDCl$_3$): δ 1.20-1.40 (br m, 14H), 1.55-1.78 (m, 2H), 1.97-2.07 (m, 2H), 2.16 (s, 1H), 3.75 (S, 6H), 3.76-3.85 (m, 2H), 4.18 (ddd, J=2.2, 5.3, 8.74 Hz, 1H), 4.26 (ddd, J=3.9, 5.3, 8.74 Hz, 1H), 4.52 (dd, J=1.3, 2.2 Hz, 1H), 4.71 (br dd, J=1.3, 3.3 Hz, 1H), 4.91 (ddd, J=1.2, 2.6, 10.2 Hz, 1H), 4.98

(ddd, J=1.4, 2.6, 17.0 Hz, 1H), 5.80 (ddt, J=6.7, 10.2, 17.0 Hz, 1H), 6.78-6.83 (br m, 8H); $^{13}$C NMR (100 MHz, CDCl$_3$): 25.8 (t), 29.0 (t), 29.2 (t), 29.4 (t), 29.5 (t, 3C), 32.4 (t), 33.8 (t), 55.7 (q, 2C), 62.4 (t), 82.8 (d), 83.2 (d), 83.3 (d), 86.5 (d), 114.1 (t), 114.8 (d, 4C), 117.0 (d, 2C), 117.2 (d, 2C), 139.26 (d), 151.1 (s), 151.2 (s), 154.6 (s), 158.0 (s) ppm; ESI-MS: Anal. (C$_{30}$H$_{42}$O$_6$) 521.64 ([M+Na]$^+$

Example 21: 2,3-Di-O-(1-naphthyl)-10-α-D-Arabinofuranosylundecene (20)

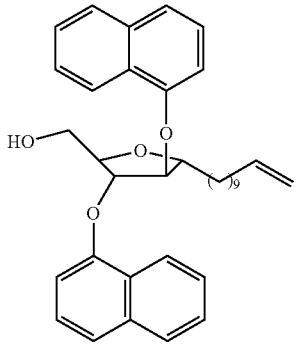

$^1$H NMR (400 MHz, CDCl$_3$): δ 1.20-1.40 (br m, 14H), 1.53-186 (m, 2H), 1.98-2.07 (m, 2H), 2.15 (br s, 1H, —OH), 3.96 (d, J=4.7 Hz, 2H), 4.44 (ddd, J=1.6, 5.3, 7.9 Hz, 1H), 4.52 (ddd, J=2.9, 4.6, 7.9 Hz, 1H), 4.92 (ddd, J=1.2, 3.5, 10.2 Hz, 1H), 4.98 (ddd, J=1.6, 3.6, 17.0 Hz, 1H), 5.00 (br s, 1H), 5.23 (d, J=3.0 Hz, 1H), 5.8 (ddt, J=6.6, 10.2, 17.0 Hz, 1H), 6.72 (d, J=7.6 Hz, 1H), 6.86 (d, J=7.6 Hz, 1H), 7.25 (t, J=8.3 Hz, 1H), 7.26 (t, J=7.8 Hz, 1H), 7.42-7.58 (m, 6H), 7.75-7.85 (m, 2H), 8.28 (dd, J=3.0, 5.8 Hz, 1H), 8.32 (dd, J=3.0, 5.8 Hz, 1H); $^{13}$C NMR (100 MHz, CDCl$_3$): δ 25.7 (t), 28.9 (t), 29.1 (t), 29.4 (t), 29.5 (t, 3C), 32.3 (t), 33.8 (t), 62.4 (t), 82.7 (d), 83.1 (d), 83.4 (d), 85.6 (d), 106.1 ( ), 106.3 ( ), 114.1 (t), 121.2 (d, 2C), 121.7 (d), 121.8 (d), 125.5 (d), 125.6 (d), 125.7 (d), 125.7 (d), 125.8 (d), 125.8 (d), 126.6 (d), 126.7 (d), 127.6 (d, 2C), 134.7 (d, 2C), 139.2 (d), 152.6 (s), 152.7 (s) ppm; ESI-MS: Anal. (C$_{36}$H$_{42}$O$_4$) 561.32 [M+Na]$^+$.

Example 22: 2,3-Di-O-(3-nitro phenyl)-10-α-D-Arabinofuranosylundecene (21)

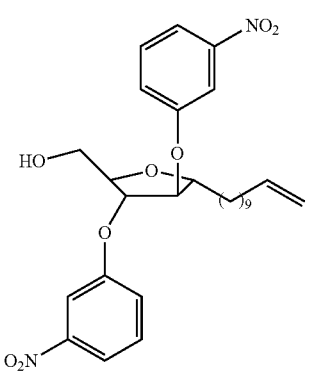

[α]$_D^{26}$: +8.5 (c 2.3, CHCl$_3$); $^1$H NMR (400 MHz, CDCl$_3$): δ 1.20-1.48 (br m, 14H), 1.71-1.87 (m, 2H), 1.98-2.10 (m, 2H), 2.14 (br s, 1H, —OH), 3.78-3.90 (br m, 2H), 3.96 (dd, J=4.2, 11.7 Hz, 1H), 4.26 (ddd, J=3.1, 5.3, 8.7 Hz, 1H), 4.31 (dd, J=4.4, 8.7 Hz, 1H), 4.75 (dd, J=1.9, 2.8 Hz, 1H), 4.87-5.07 (br m, 3H), 5.85 (ddt, J=6.6, 10.2, 17.0 Hz, 1H), 7.23-7.36 (br m, 2H), 7.45 (t, J=8.2 Hz, 1H), 7.46 (t, J=8.2 Hz, 1H), 7.75 (t, J=2.2 Hz, 1H), 7.82-7.90 (br m, 3H); $^{13}$C NMR (100 MHz, CDCl$_3$): 25.6 (t), 28.9 (t), 29.1 (t), 29.3 (t), 29.4 (t, 3C), 32.4 (t), 33.8 (t), 61.7 (t), 81.9 (d), 82.6 (d), 82.8 (d), 86.6 (d), 109.8 (d), 110.1 (d), 114.1 (t), 116.9 (d, 2C), 122.2 (d), 122.6 (d), 130.4 (d, 2C), 139.22 (d), 149.2 (s, 2C), 157.5 (s, 2C) ppm; ESI-MS: Anal. (C$_{28}$H$_{36}$N$_2$O$_8$) 551.32 [M+Na]$^+$

Example 23: 2,3-Di-O-(4-nitro phenyl)-10-α-D-Arabinofuranosylundecene (22)

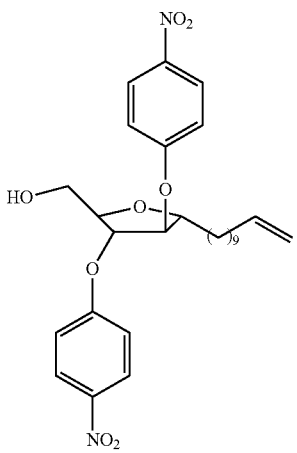

[α]$_D^{26}$: +35.8 (c 2.6, CHCl$_3$); $^1$H NMR (400 MHz, CDCl$_3$): δ 1.20-1.48 (br m, 14H), 1.57-1.75 (m, 2H), 1.97-2.07 (m, 2H), 2.16 (s, 1H, —OH), 3.75-3.90 (br m, 2H), 3.94 (dd, J=4.4, 11.7 Hz, 1H), 4.21 (br dd, J=2.5, 4.9 Hz, 1H), 4.28 (dd, J=4.4, 8.5 Hz, 1H), 4.75 (br s, 1H), 4.85-5.10 (br m, 3H), 5.79 (ddt, J=6.7, 10.2, 17.0 Hz, 1H), 6.95 (d, J=9.2 Hz, 2H), 7.05 (d, J=9.2 Hz, 2H), 8.15 (d, J=1.2 Hz, 2H), 8.19 (d, J=1.2 Hz, 2H); $^{13}$C NMR (100 MHz, CDCl$_3$): 25.6 (t), 28.9 (t), 29.1 (t), 29.3 (t), 29.4 (t, 3C), 32.3 (t), 33.7 (t), 61.6 (t), 82.0 (d), 82.6 (d), 82.8 (d), 86.5 (d), 114.1 (t), 115.4 (d, 4C), 126.1 (d, 4C), 139.1 (d), 142.3 (s, 2C), 161.7 (s, 2C), 161.8 (s, 2C) ppm; ESI-MS: Anal. (C$_{28}$H$_{36}$N$_2$O$_8$) 551.33 [M+Na]$^+$

Example 24: 2,3-Di-O-(3-methyl phenyl)-10-α-D-Arabinofuranosylundecene (23)

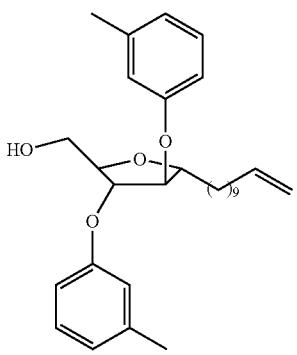

[α]$_D^{26}$: +11.6 (c 1.2, CHCl$_3$); $^1$H NMR (400 MHz, CDCl$_3$): δ 1.20-1.48 (br m, 14H), 1.59-1.79 (m, 2H), 1.99-2.16 (m, 2H), 2.28 (s, 6H), 3.78-3.88 (br m, 2H), 4.16-4.25

(br m, 2H), 4.29 (dd, J=4.4, 8.5 Hz, 1H), 4.62 (br s, 1H), 4.80 (d, J=2.9 Hz, 1H), 4.87-5.07 (br m, 2H), 5.81 (ddt, J=6.7, 10.1, 17.0 Hz, 1H), 6.68 (d, J=2.2 Hz, 2H), 6.72 (d, J=7.0 Hz, 2H), 7.70 (d, J=6.8 Hz, 2H), 7.14 (t, J=7.6 Hz, 2H); $^{13}$C NMR (100 MHz, CDCl$_3$): 21.4 (q, 2C), 25.8 (t), 28.9 (t), 29.1 (t), 29.4 (t), 29.5 (t, 3C), 32.2 (t), 33.8 (t), 61.3 (t), 82.4 (d), 83.0 (d), 83.4 (d), 85.5 (d), 112.5 (d), 112.6 (d), 114.1 (t), 116.6 (d), 116.8 (d), 122.5 (d), 129.4 (d), 139.2 (d), 139.8 (d, 2C), 157.0 (s), 157.2 (s) ppm; ESI-MS: Anal. (C$_{30}$H$_{42}$O$_4$) 489.29 [M+Na]$^+$ Example 25: 2,3-Di-O-(4-methyl phenyl)-10-α-D-Arabinofuranosylundecene (24)

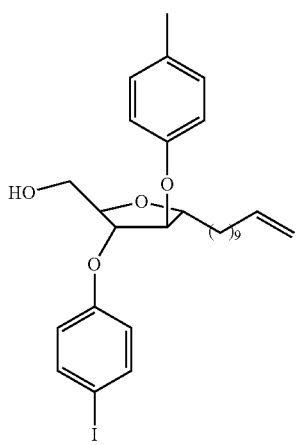

$[\alpha]_D^{26}$: +22.44 (c 3.8, CHCl$_3$); $^1$H NMR (400 MHz, CDCl$_3$): δ 1.20-1.48 (br m, 14H), 1.59-1.84 (m, 2H), 1.98-2.10 (m, 2H), 2.27 (s, 6H), 3.78-3.88 (br m, 2H), 4.16-4.24 (br m, 2H), 4.27 (dd, J=4.0, 8.6 Hz, 1H), 4.59 (br s, 1H), 4.77 (d, J=3 Hz, 1H), 4.86-5.06 (br m, 2H), 5.81 (ddt, J=6.7, 10.1, 17.0 Hz, 1H), 6.77 (d, J=6.7 Hz, 2H), 6.81 (d, J=6.7 Hz, 2H), 7.05 (d, J=8.4 Hz, 4H); $^{13}$C NMR (100 MHz, CDCl$_3$): 20.4 (q, 2C), 25.8 (t), 28.9 (t), 29.1 (t), 29.4 (t), 29.5 (t, 3C), 32.2 (t), 33.8 (t), 62.3 (t), 82.5 (d), 82.9 (d), 83.2 (d), 85.6 (d), 114.1 (t), 115.5 (d, 2C), 115.7 (d, 2C), 130.1 (d, 4C), 130.9 (s, 2C), 139.2 (d), 154.8 (s), 155.0 (s) ppm; ESI-MS: Anal. (C$_{30}$H$_{42}$O$_4$) 489.31 [M+Na]$^+$ Example 26: O-(3-fluro phenyl)-10-α-D-Arabinofuranosylundecene (25)

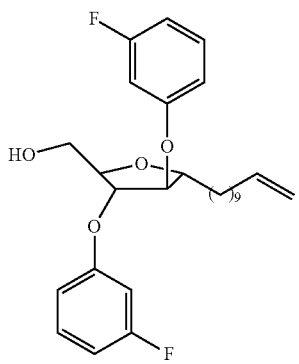

$[\alpha]_D^{26}$: +2.4 (c 8.4, CHCl$_3$); $^1$H NMR (400 MHz, CDCl$_3$): δ 1.20-1.45 (br m, 14H), 1.59-1.82 (m, 2H), 1.97-2.11 (m, 2H), 2.24 (s, 1H), 3.77 (br dd, J=5.5, 11.7 Hz, 1H), 3.89 (br dd, J=4.6, 11.9 Hz, 1H), 4.19 (dd, J=2.3, 5.3 Hz, 1H), 4.27 (dd, J=4.4, 8.7 Hz, 1H), 4.62 (dd, J=1.3, 2.2 Hz, 1H), 4.83 (d, J=3.0 Hz, 1H), 4.88-5.06 (br m, 2H), 5.81 (ddt, J=6.7, 10.1, 17.0 Hz, 1H), 6.60-6.75 (br m, 6H), 7.17 (d, J=7.9 Hz, 2H), 7.24 (t, J=7.6 Hz, 2H); $^{13}$C NMR (100 MHz, CDCl$_3$): 25.8 (t), 28.9 (t), 29.1 (t), 29.3 (t), 29.4 (t, 3C), 32.2 (t), 33.8 (t), 61.9 (t), 82.4 (d), 82.5 (d), 83.0 (d), 86.0 (d), 103.4 (d, J=2.5 Hz, 1C), 103.9 (d, J=2.5 Hz, 1C), 103.6 (d, J=25 Hz, 1C), 103.7 (d, J=25 Hz, 1C), 108.7 (d, J=21.2 Hz, 2C), 111.0 (d, J=2.8 Hz, 1C), 111.2 (d, J=2.8 Hz, 1C), 130.5 (d, J=9.9 Hz, 1C), 139.2 (s), 158.2 (d, J=10.7 Hz, 1C), 158.3 (d, J=10.7 Hz, 1C), 163.0 (d, J=246.6 Hz, 1C), ppm; ESI-MS: Anal. (C$_{28}$H$_{36}$F$_2$O$_4$) 497.26 [M+Na]$^+$ Example 27: 2,3-Di-O-methyl-10-α-D-Arabinofuranosylundecene (26)

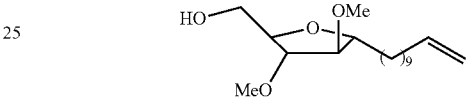

$[\alpha]_D^{\sim}$: +33.6 (c 2.6, CHCl$_3$); $^1$H NMR (400 MHz, CDCl$_3$): δ 1.20-1.40 (br m, 14H), 1.53-1.70 (m, 2H), 1.97-2.07 (m, 2H), 2.16 (br s, 1H, —OH), 3.37 (s, 3H), 3.38 (s, 3H), 3.47-3.55 (br m, 1H),), 3.66-3.75 (br m, 3H), 3.91 (br dd, J=3.4, 8.3 Hz, 1H), 3.99 (dd, J=4.0, 8.2 Hz, 1H), 4.85-5.06 (br m, 2H), 5.85 (ddt, J=6.7, 10.0, 17.0 Hz, 1H); $^{13}$C NMR (100 MHz, CDCl$_3$): 25.8 (t), 28.9 (t), 29.1 (t), 29.5 (t, 4C), 33.0 (t), 33.8 (t), 57.3 (q), 57.7 (q), 62.9 (t) 82.4 (t), 82.8 (t), 86.3 (d), 89.3 (d), 114.1 (t), 139.2 (d) ppm; ESI-MS: Anal. (C$_{18}$H$_{34}$O$_4$) 314.46 [M+Na]$^+$.

Example 28: 2,3-Di-O-octyl-10-α-D-Arabinofuranosylundecene (27)

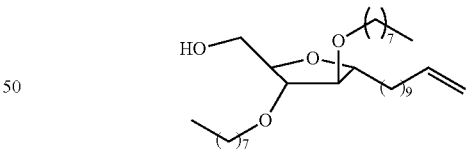

$[\alpha]_D^{26}$: +22.2 (c 2.1, CHCl$_3$); $^1$H NMR (400 MHz, CDCl$_3$): δ 0.9 (t, J=6.6, Hz), 1.20-1.40 (br m, 34H), 1.48-1.65 (m, 6H), 1.97-2.08 (br m, 2H), 3.39-3.52 (br m, 4H), 3.59 (dd, J=2.6, 3.2 Hz, 1H), 3.69 (dd, J=6.3, 11.0 Hz, 1H), 3.73 (dd, J=2.4, 4.0 Hz, 1H), 3.90 (ddd, J=3.6, 5.6, 8.5 Hz, 1H), 3.99 (ddd, J=4.0, 5.0, 9.0 Hz, 1H), 4.65 (br m, 1H), 4.86-5.05 (br m, 2H), 5.80 (ddt, J=6.7, 10.0, 16.9 Hz, 1H); $^{13}$C NMR (100 MHz, CDCl$_3$): 14.1 (q, 2C), 22.6 (t, 2C), 25.9 (t), 26.1 (t, 2C), 28.9 (t), 29.1 (t), 29.3 (t, 2C), 29.4 (t, 2C), 29.5 (t, 4C), 29.8 (t), 31.8 (t, 3C), 331 (t), 33.81 (t), 63.1 (t), 69.9 (t), 70.2 (t), 82.6 (d), 82.9 (d), 85.0 (d), 87.8 (d), 114.1 (t), 139.2 (d) ppm; ESI-MS: Anal. (C$_{32}$H$_{62}$O$_4$) 533.56 [M+Na]$^+$.

Example 29: 10-α-D-Arabinofuranosylundecane (28)

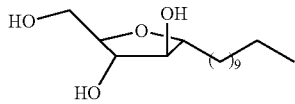

¹H NMR (400 MHz, CDCl₃): δ δ 0.9 (t, J=6.6, Hz), 1.20-1.40 (br m, 14H), 1.56-1.64 (m, 2H), 1.99-2.08 (m, 2H), 2.16 (br s, 1H, —OH), 3.68-3.70 (m, 2H), 3.82 (dd, J=0.7, 2.6 Hz, 1H), 3.96-4.04 (br m, 2H), 4.09 (dd, J=4.3, 9.2 Hz, 1H), 4.53 (s, 2H), 4.55 (s, 2H); ¹³C NMR (100 MHz, CDCl₃): 14.3 (q), 25.6 (t), 28.8 (t), 29.0 (t), 29.4 (t, 3C), 32.9 (t), 33.7 (t, 2C), 62.6 (t), 71.5 (t), 71.9 (t), 82.6 (d), 82.7 (d), 84.4 (d), 87.2 (d) ppm; ESI-MS: Anal. (C₁₆H₃₂O₄) 311.46 ([M+Na]⁺.

Example 30: 2,3-Di-O-benzyl-10-β-D-Arabinofuranosylundecene (29)

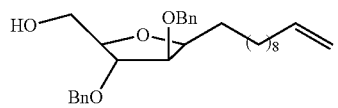

¹H NMR (400 MHz, CDCl₃): δ 1.21-1.44 (br m, 14H), 1.56-1.64 (m, 2H), 1.99-2.08 (m, 2H), 2.16 (br s, 1H, —OH), 3.69-3.71 (m, 2H), 3.82 (m, 1H), 4.00-4.14 (br m, 2H), 4.18 (m, 1H), 4.55 (s, 2H), 4.57 (s, 2H), 4.93-5.09 (br m, 2H), 5.88 (ddt, J=6.7, 10.2, 16.9 Hz, 1H), 7.30-7.42 (br m, 10H); ¹³C NMR (100 MHz, CDCl₃): 25.7 (t), 28.9 (t), 29.0 (t), 29.5 (t, 3C), 33.0 (t), 33.8 (t, 2C), 63.0 (t), 71.4 (t), 71.8 (t), 82.3 (d), 82.6 (d), 84.4 (d), 87.0 (d), 114.1 (t), 127.5 (d), 127.6 (d, 2C), 127.7 (d), 128.3 (t, 2C), 128.3 (t, 2C), 137.5 (s), 137.6 (s), 139.0 (s); ESI-MS: Anal. (C₃₀H₄₂O₄) 505.67 ([M+K]⁺

Example 31: 2,3-Di-O-phenyl-10-β-D-Arabinofuranosylundecene (30)

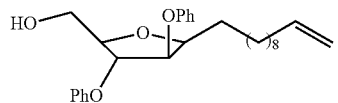

¹H NMR (400 MHz, CDCl₃): δ 1.21-1.41 (br m, 16H), 1.99-2.10 (m, 2H), 2.16 (br s, 1H, —OH), 3.80-3.90 (m, 2H), 4.20-4.25 (m, 1H), 4.28-4.36 (m, 1H), 4.68-4.90 (br m, 1H), 4.87-4.89 (m, 1H), 4.94 (ddd, J=1.2, 3.5, 10.2 Hz, 1H), 4.95 (ddd, J=1.6, 3.5, 16.5 Hz, 1H), 5.86 (ddt, J=6.6, 10.2, 16.5 Hz, 1H), 6.66-7.07 (m, 6H), 7.24-7.35 (m, 4H); ¹³C NMR (100 MHz, CDCl₃): 25.7 (t), 28.9 (t), 29.1 (t), 29.4 (t), 29.5 (t, 3C), 32.2 (t), 33.8 (t), 62.6 (t), 81.1 (d), 80.8 (d), 82.2 (d), 88.4 (d), 114.1 (t), 115.7 (d, 2C), 115.8 (d, 2C), 121.7 (d, 2C), 129.7 (d, 4C), 139.2 (s), 157.0 (s), 157.1 (s) ppm; ESI-MS: Anal. (C₂₈H₃₈O₄) 461.66 [M+Na]⁺.

Example 32: 2,3-Di-O-(4-methyoxy phenyl)-10-β-D-Arabinofuranosylundecene (31)

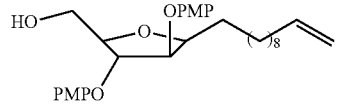

[α]_D: +29.7.1 (c 2.3, CHCl₃); ¹H NMR (400 MHz, CDCl₃): δ 1.20-1.40 (br m, 14H), 1.55-1.81 (m, 2H), 1.97-2.07 (m, 2H), 2.17 (s, 1H), 3.76 (S, 6H), 3.77-3.86 (m, 2H), 4.19-4.25 (m, 1H), 4.22-4.28 (m, 1H), 4.62-4.65 (m, 1H), 4.85-4.88 (m, 1H), 4.93 (ddd, J=1.2, 2.6, 10.2 Hz, 1H), 5.00 (ddd, J=1.4, 2.6, 17.0 Hz, 1H), 5.85 (ddt, J=6.7, 10.2, 17.0 Hz, 1H), 6.81-6.86 (br m, 8H); ¹³C NMR (100 MHz, CDCl₃): 25.80 (t), 28.95 (t), 29.15 (t), 29.41 (t), 29.52 (t, 3C), 32.37 (t), 33.83 (t), 55.7 (q, 2C), 62.7 (t), 82.5 (d), 81.2 (d), 82.3 (d), 89.3 (d), 114.13 (t), 113.5 (d, 4C), 117.0 (d, 2C), 117.21 (d, 2C), 139:26 (d), 151.05 (s), 151.22 (s), 154.57 (s), 158.01 (s) ppm; ESI-MS: Anal. (C₃₀H₄₂O₆) 521.77 [M+Na]⁺.

Example 33: 2,3-Di-O-(1-naphthyl)-10-β-D-Arabinofuranosylundecene (32)

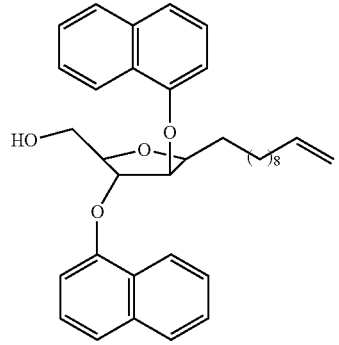

¹H NMR (400 MHz, CDCl₃): δ 1.21-1.42 (br m, 14H), 1.54-187 (m, 2H), 1.98-2.07 (m, 2H), 2.17 (br s, 1H, –OH), 3.93-3.98 (m, 2H), 4.42-4.45 (m, 1H), 4.58-5.12 (m, 1H), 5.13-5.16 (m, 1H), 5.22 (ddd, J=1.6, 3.6, 17.0 Hz, 1H), 5.30 (br s, 1H), 5.55-5.73 (m, 1H), 5.8 (ddt, J=6.6, 10.2, 17.0 Hz, 1H), 6.73 (d, J=7.6 Hz, 1H), 6.89 (d, J=7.6 Hz, 1H), 7.26 (t, J=8.3 Hz, 1H), 7.28 (t, J=7.8 Hz, 1H), 7.45-7.62 (m, 6H), 7.78-7.88 (m, 2H), 8.32 (dd, J=3.0, 5.8 Hz, 1H), 8.36 (dd, J=3.0, 5.8 Hz, 1H); ¹³C NMR (100 MHz, CDCl₃): δ 25.8 (t), 29.0 (t), 29.2 (t), 29.6 (t), 29.6 (t, 3C), 32.4 (t), 33.9 (t), 62.7 (t), 82.4 (d), 81.0 (d), 82.6 (d), 88.4 (d), 106.1 (d), 106.3 (d), 113.5 (t), 121.3 (d, 2C), 121.8 (d), 121.9 (d, 2C), 125.6 (d), 125.7 (d), 125.8 (d), 125.9 (d), 125.8 (d), 125.8 (d), 126.6 (d), 126.7 (d), 127.6 (d, 2C), 134.7 (d, 2C), 139.2 (s), 152.6 (s), 152.7 (s) ppm; ESI-MS: Anal. (C₃₆H₄₂O₄) 561.33 [M+Na]⁺.

Example 34: 2,3-Di-O-(3-nitro phenyl)-10-β-D-Arabinofuranosylundecene (33)

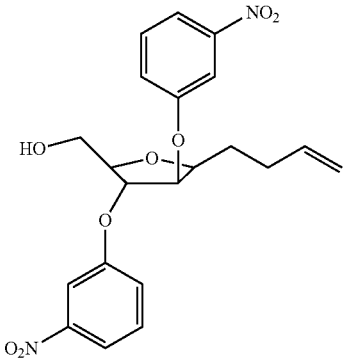 [SMILES: C=CCCC1OC(CO)C(Oc2cccc([N+](=O)[O-])c2)C1Oc1cccc([N+](=O)[O-])c1]

$^1$H NMR (400 MHz, CDCl$_3$): δ 1.19-1.50 (br m, 14H), 1.69-1.85 (m, 2H), 1.97-2.07 (m, 2H), 2.17 (br s, 1H, —OH), 3.74-3.92 (br m, 2H), 3.94-3.97 (m, 1H), 4.24-4.27 (m, 1H), 4.36-4.39 (m, 1H), 5.01-5.07 (m, 1H), 4.87-5.07 (br m, 3H), 5.86 (ddt, J=6.6, 10.2, 17.0 Hz, 1H), 7.24-7.37 (br m, 2H), 7.46 (t, J=8.2 Hz, 1H), 7.47 (t, J=8.2 Hz, 1H), 7.76 (t, J=2.2 Hz, 1H), 7.83-7.91 (br m, 3H); $^{13}$C NMR (100 MHz, CDCl$_3$): 25.7 (t), 28.8 (t), 29.1 (t), 29.2 (t), 29.3 (t, 3C), 32.5 (t), 33.7 (t), 61.9 (t), 81.6 (d), 80.5 (d), 81.8 (d), 89.5 (d), 109.9 (d), 110.2 (d), 114.2 (t), 116.9 (d, 2C), 122.2 (d), 122.6 (d), 130.4 (d, 2C), 139.22 (d), 149.2 (s, 2C), 157.5 (s, 2C) ppm; ESI-MS: Anal. (C$_{28}$H$_{36}$N$_2$O$_8$) 551.67 [M+Na]$^+$

Example 35: 2,3-Di-O-(4-nitro phenyl)-10-β-D-Arabinofuranosylundecene (34)

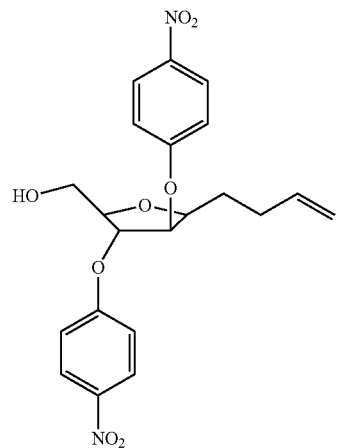 [SMILES: C=CCCC1OC(CO)C(Oc2ccc([N+](=O)[O-])cc2)C1Oc1ccc([N+](=O)[O-])cc1]

$^1$H NMR (400 MHz, CDCl$_3$): δ 1.18-1.46 (br m, 14H), 1.48-1.66 (m, 2H), 1.96-2.04 (m, 2H), 2.17 (s, 1H, —OH), 3.74-3.91 (br m, 2H), 3.94-396 (m, 1H), 4.21-4.26 (m, 1H), 4.28-4.30 (m, 1H), 4.75 (br s, 1H), 4.85-5.10 (br m, 3H), 5.81 (ddt, J=6.6, 10.3, 17.1 Hz, 1H), 6.98 (d, J=9.2 Hz, 2H), 7.08 (d, J=9.2 Hz, 2H), 8.18 (d, J=1.2 Hz, 2H), 8.21 (d, J=1.2 Hz, 2H); $^{13}$C NMR (100 MHz, CDCl$_3$): 25.7 (t), 29.0 (t), 29.2 (t), 29.4 (t), 29.5 (t, 3C), 32.2 (t), 33.6 (t), 62.0 (t), 80.7 (d), 81.8 (d), 81.9 (d), 89.1 (d), 115.5 (t), 115.6 (d, 4C), 126.2 (d, 4C), 139.3 (d), 142.2 (s, 2C), 161.6 (s, 2C), 161.9 (s, 2C) ppm; Anal. (C$_{28}$H$_{36}$N$_2$O$_8$) 551.44 [M+Na]$^+$

Example 36: 2,3-Di-O-(3-methyl phenyl)-10-β-D-Arabinofuranosylundecene (35)

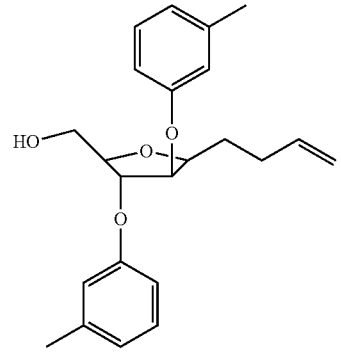 [SMILES: C=CCCC1OC(CO)C(Oc2cccc(C)c2)C1Oc1cccc(C)c1]

$^1$H NMR (400 MHz, CDCl$_3$): δ 1.18-1.46 (br m, 14H), 1.57-1.77 (m, 2H), 1.97-2.14 (m, 2H), 2.30 (s, 6H), 3.80-3.87 (br m, 2H), 4.13-4.22 (br m, 2H), 4.27-4.29 (m, 1H), 4.62 (br s, 1H), 4.78-4.82 (m, 1H), 4.87-5.07 (br m, 2H), 5.80-5.83 (m, 1H), 6.67 (m, 2H), 6.73 (m, 2H), 7.70 (m, 2H), 7.74 (m, 2H); $^{13}$C NMR (100 MHz, CDCl$_3$): 21.3 (q, 2C), 25.9 (t), 28.8 (t), 29.2 (t), 29.6 (t), 29.8 (t, 3C), 32.3 (t), 33.9 (t), 62.7 (t), 82.2 (d), 81.0 (d), 82.5 (d), 88.1 (d), 112.6 (d), 112.7 (d), 114.2 (t), 116.6 (d), 116.8 (d), 122.5 (d), 129.4 (d), 139.4 (d), 139.8 (d, 2C), 157.0 (s), 157.2 (s) ppm; ESI-MS: Anal. (C$_{30}$H$_{42}$O$_4$) 489.31 [M+Na]$^+$

Example 37: 2,3-Di-O-(4-methyl phenyl)-10-β-D-Arabinofuranosylundecene (36)

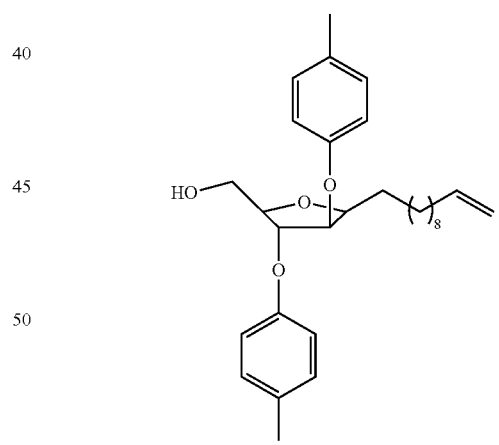

$^1$H NMR (400 MHz, CDCl$_3$): δ 1.23-1.53 (br m, 14H), 1.63-1.89 (m, 2H), 210-2.20 (m, 2H), 2.29 (s, 6H), 3.75-3.86 (br m, 2H), 4.16-4.24 (br m, 2H), 4.27 (m, 1H), 4.59 (br s, 1H), 4.77 (m, 1H), 4.88-5.09 (br m, 2H), 5.83 (ddt, J=6.6, 10.2, 16.9 Hz, 1H), 6.79 (d, J=6.8 Hz, 2H), 6.85 (d, J=6.8 Hz, 2H), 7.05 (d, J=6.9 Hz, 4H); $^{13}$C NMR (100 MHz, CDCl$_3$): 20.6 (q, 2C), 25.9 (t), 29.0 (t), 29.3 (t), 29.6 (t), 29.7 (t, 3C), 32.4 (t), 33.9 (t), 62.37 (t), 80.9 (d), 82.4 (d), 82.3 (d), 88.6 (d), 114.2 (t), 115.8 (d, 2C), 116.0 (d, 2C), 130.4 (d, 4C), 131.2 (s, 2C), 139.4 (d), 155.2 (s), 155.0 (s) ppm; ESI-MS: Anal. (C$_{30}$H$_{42}$O$_4$) 489.39 [M+Na]$^+$

Example 38: 2,3-Di-O-(3-fluro phenyl)-10-β-D-Arabinofuranosylundecene (37)

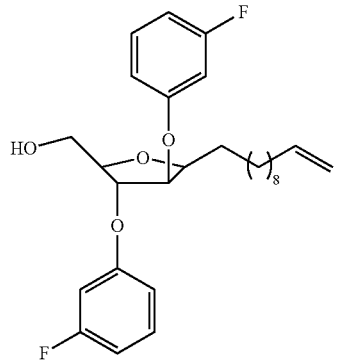

$^1$H NMR (400 MHz, CDCl$_3$): δ 1.21-1.46 (br m, 14H), 1.61-1.83 (m, 2H), 1.997-2.13 (m, 2H), 2.17 (s, 1H), 3.80-3.85 (m, 1H), 3.87-3.89 (m, 1H), 4.17-4.20 (m, 1H), 4.22-4.26 (m, 1H), 4.58-4.63 (m, 1H), 4.80-4.85 (m, 1H), 4.88-5.06 (br m, 2H), 5.81 (ddt, J=6.7, 10.1, 17.0 Hz, 1H), 6.61-6.76 (br m, 6H), 7.18 (d, J=7.9 Hz, 2H), 7.25 (t, J=7.6 Hz, 2H); $^{13}$C NMR (100 MHz, CDCl$_3$): 24.9 (t), 29.0 (t), 29.3 (t), 29.4 (t), 29.6 (t, 3C), 32.6 (t), 33.9 (t), 62.4 (t), 80.6 (d), 82.0 (d), 82.3 (d), 89.0 (d), 103.6 (d, J=2.5 Hz, 1C), 104.1 (d, J=2.5 Hz, 1C), 103.8 (d, J=25 Hz, 1C), 103.9 (d, J=25 Hz, 1C), 108.9 (d, J=21.2 Hz, 2C), 111.2 (d, J=2.8 Hz, 1C), 111.4 (d, J=2.8 Hz, 1C), 114.2 (d), 130.7 (d, J=9.9 Hz, 1C), 139.3 (s), 158.4 (d, J=10.7 Hz, 1C), 158.5 (d, J=10.7 Hz, 1C), 163.2 (d, J=246.6 Hz, 1C), ppm; ESI-MS: Anal. (C$_{28}$H$_{36}$F$_2$O$_4$) 497.29 [M+Na]$^+$

Example 39: 2,3-Di-O-methyl-10-β-D-Arabinofuranosylundecene (38)

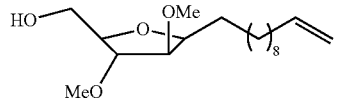

$^1$H NMR (400 MHz, CDCl$_3$): δ 1.21-1.43 (br m, 14H), 1.55-1.71 (m, 2H), 1.20-2.10 (m, 2H), 2.17 (br s, 1H, —OH), 3.39 (s, 3H), 3.40 (s, 3H), 3.47-3.55 (br m, 1H), 3.72-3.89 (br m, 3H), 3.94-3.98 (m, 1H), 4.12-4.14 (m, 1H), 4.86-5.10 (br m, 2H), 5.86 (ddt, J=6.7, 10.0, 17.0 Hz, 1H); $^{13}$C NMR (100 MHz, CDCl$_3$): 25.7 (t), 29.0 (t), 29.3 (t), 29.6 (t, 4C), 33.2 (t), 33.9 (t), 57.4 (q), 57.8 (q), 63.3 (t), 80.8 (t), 82.2 (t), 85.4 (d), 92.3 (d), 114.2 (t), 139.4 (d) ppm; ESI-MS: Anal. (C$_{18}$H$_{34}$O$_4$) 314.53 [M+Na]$^+$.

Example 40: 2,3-Di-O-octyl-10-β-D-Arabinofuranosylundecene (39)

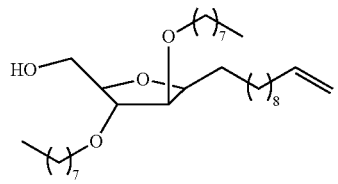

$^1$H NMR (400 MHz, CDCl$_3$): δ 1.0 (t, J=6.7, Hz), 1.21-1.48 (br m, 34H), 1.50-1.67 (m, 6H), 2.00-2.11 (br m, 2H), 3.40-3.53 (br m, 4H), 3.58-3.60 (m, 1H), 3.67-3.69 (m, 1H), 3.70-3.73 (m, 1H), 3.89-3.92 (m, 1H), 3.97-3.99 (m, 1H), 4.63-4.65 (br m, 1H), 4.86-5.05 (br m, 2H), 5.80 (ddt, J=6.7, 10.0, 16.9 Hz, 1H); $^{13}$C NMR (100 MHz, CDCl$_3$): 14.2 (q, 2C), 22.7 (t, 2C), 26.0 (t), 26.3 (t, 2C), 29.0 (t), 29.2 (t), 29.3 (t, 2C), 29.5 (t, 2C), 29.6 (t, 4C), 29.9 (t), 32.0 (t, 3C), 33.2 (t), 33.8 (t), 63.3 (t), 70.0 (t), 70.3 (t), 80.8 (d), 82.2 (d), 85.4 (d), 92.3 (d), 114.2 (t), 139.4 (d) ppm; ESI-MS: Anal. (C$_{32}$H$_{62}$O$_4$) 533.66 [M+Na]$^+$.

Example 41: 10-β-D-Arabinofuranosylundecane (40)

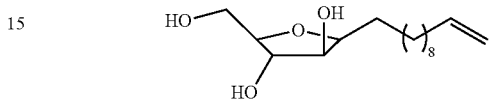

$^1$H NMR (400 MHz, CDCl$_3$): δ 1.0 (t, J=6.6 3H), 1.32-1.46 (br s, 14H), 1.63-1.67 (m, 2H), 2.03-2.08 (m, 2H), 3.64 (dd, J=4.9, 11.0 Hz, 1H), 3.69 (dd, J=4.0, 11.0 Hz, 1H), 3.74 (ddd, J=2.9, 4.0, 4.5 Hz, 1H), 3.79 (br dd, J=1.0, 3.3 Hz, 1H), 3.93 (dt, J=3.3, 7.0 Hz, 1H), 3.98 (br dd, J=1.0, 2.5 Hz, 1H), 4.93 (ddt, J=1.4, 2.5, 10.0 Hz 1H). ppm; $^{13}$C NMR (100 MHz, CDCl$_3$): 14.4 (q), 27.5 (t), 29.9 (t), 30.1 (t), 30.4 (t), 30.6 (t), 30.7 (t, 2C), 31.3 (t), 35.3 (t), 63.2 (t), 78.7 (d), 80.6 (d), 81.3 (d), 87.5 (d) ppm; ESI-MS: Anal. (C$_{16}$H$_{30}$O$_4$) 309.29 [M+Na]$^+$.

Examples

Bio-Assay

Example 42

Growth Conditions for Bacterial Strains and Cell Lines
*M. Bovis* BCG Culture:

Sub-culturing of the Strain was routinely done in Dubos albumin agar slants or plates. Liquid inoculum of the organism was added in Dubos tween albumin broth medium and incubated at 37° C. and 150 rpm shaking conditions. One percent of 1.0 O.D at 620 nm of the culture was used as standard inoculum size for all the experiments, yielding a final inoculum of approximately 105 CFU/ml. viable cell counts were measured by following an earlier described method.[1] Thp-1, MCF-7 and HL-60 cell line: Cells obtained were at passage numbers 90-93. Cells were cultured at 37° C. with 5% $CO_2$ and 90% humidity in T-75 tissue culture flasks (Corning 430641). Cells were maintained in the culture medium used Minimum Essential Medium (MEM) without phenol red with 2.5 mM L-glutamine (Sigma, US) and supplemented with 10% fetal bovine serum.

Example 43

Effect of Inhibitors on Growth of the Bacilli

The inhibitory effect of the compounds was monitored by following an earlier described method. Briefly, 247.5 μl of 1% of 1 O.D at 620 nm *M. Bovis* BCG culture was taken in Dubos medium without ADS enrichment in microplate wells. Already having 2.5 μl of inhibitor in DMSO, the plate was then covered with a sterile sealer and incubated at 37° C. for 8 days. Then the growth of the bacilli was measured by reading the absorbance at 620 nm as well as by determining CFU/ml of the culture at different time intervals. The lowest concentration of drugs yielding a differential absorbance (620 nm) of approximately zero was defined as MIC.

The well representing positive controls have only DMSO (vehicle) and the negative controls were having rifampicin and ethambutol at their respective IC$_{50}$ values. (FIG. 1)

Example 44

Cytotoxicity Assessment of the Inhibitors

Figure 2B:
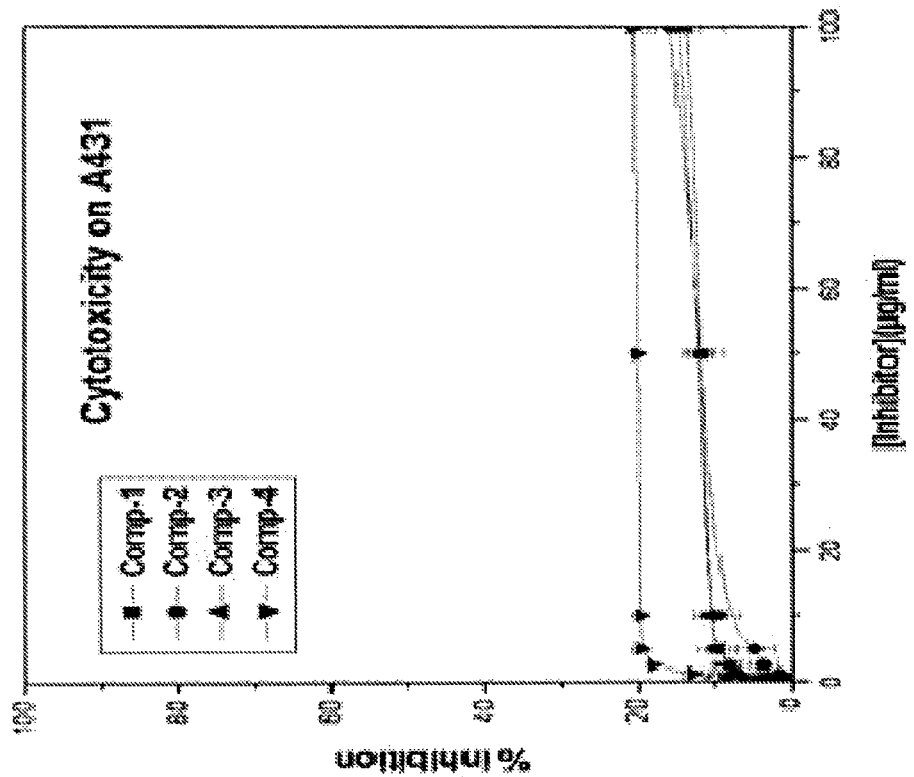
Figure 2A:
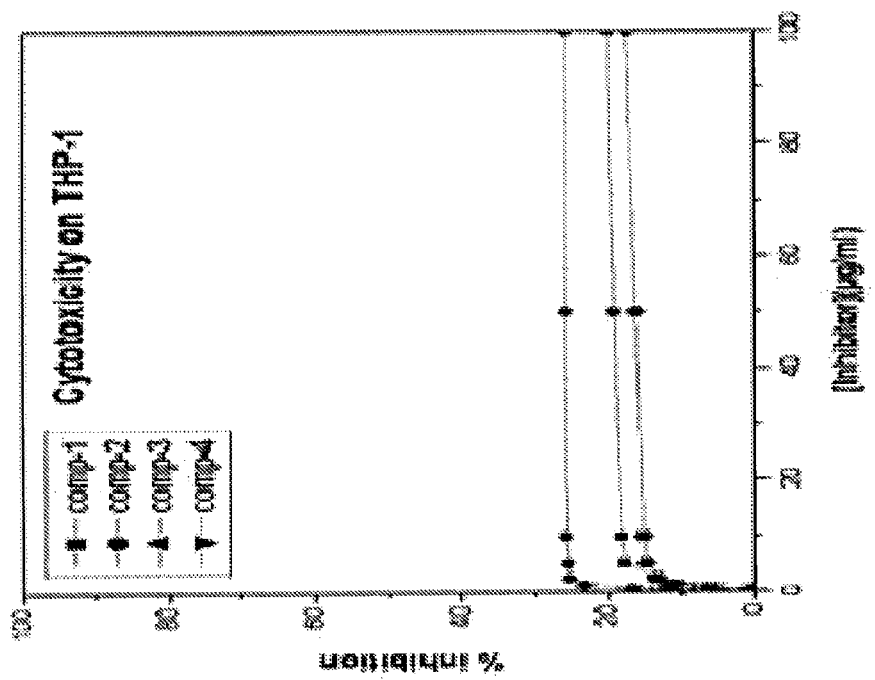
Figure 2C:
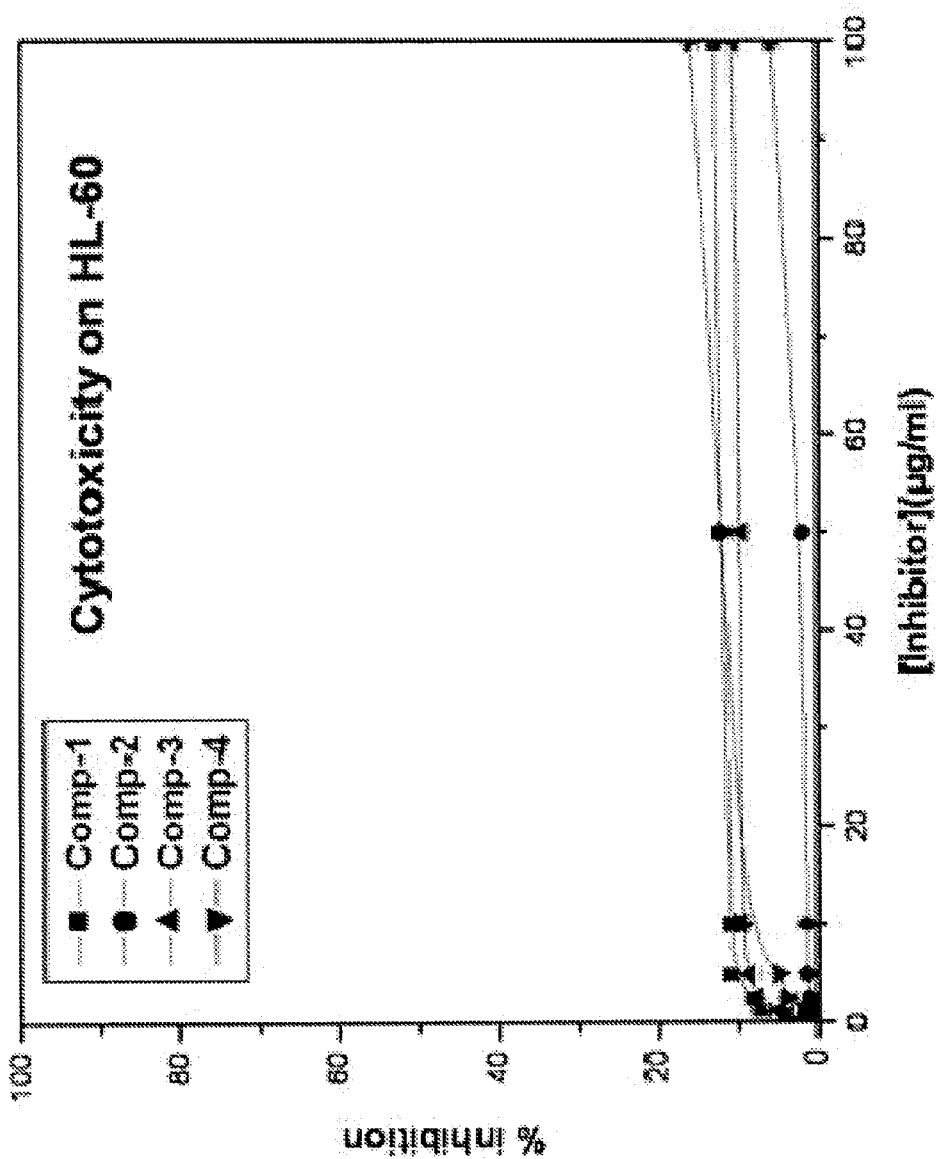
Figure 3B:
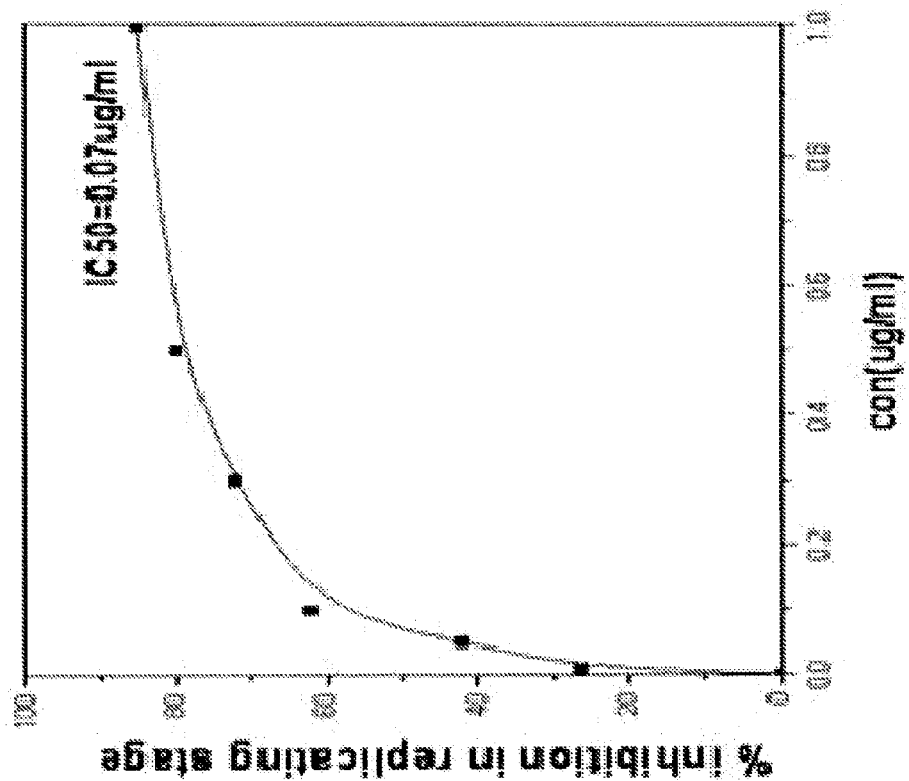
Figure 3A:
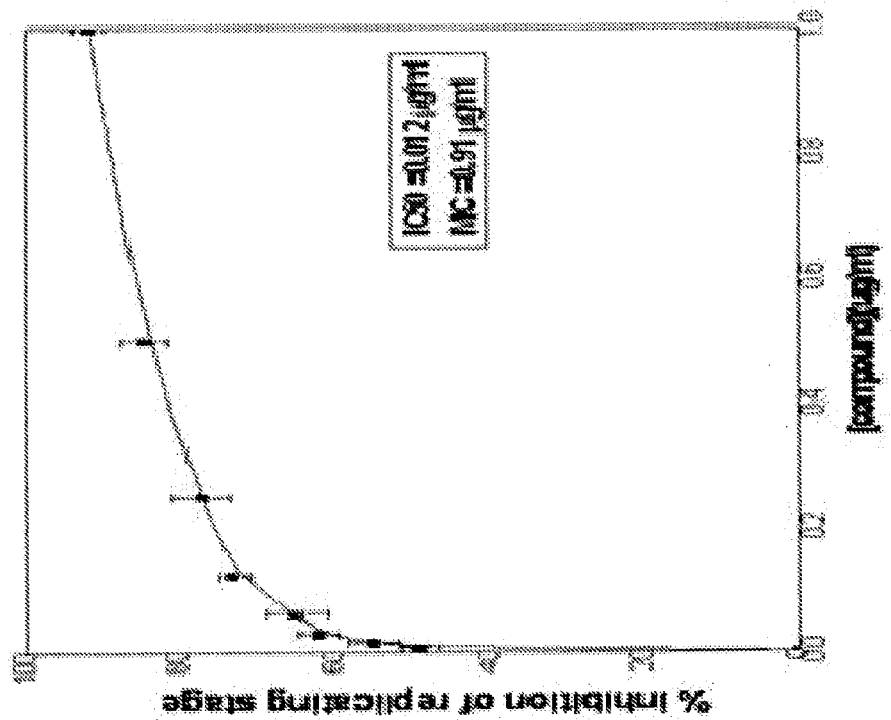

To test the in vitro viability/cytotoxicity of the compounds, THP-1, A431 and HL-60 human cell lines were selected. The effect of the compounds were examined on metabolic function of the cells using a standard MTT assay 3 a widely adopted method of measuring cellular proliferation. The MTT assay consists of a yellow tetrazolium 3-(4,5-dimethylthiazolyl)-2,5-diphenyltetrazolium bromide) dye that is reduced by mitochondrial dehydrogenase enzymes to form purple formazan which gets precipitated within viable cells. The concentration of formazan formed is proportional to the number of viable cells. These crystals of reduced MTT dye i.e. formazan, absorbs light at 490 nm. The absorbance of light at 490 nm should be proportional to the viable cell count. For this, 100 µl of the culture containing 10,000 cells/ml was added to each of the 96 wells of the tissue culture plate containing 2.5 µl of inhibitors. Then, the cells were incubated in a CO2 incubator supplied with 5% CO2, 95% humidity at 37° C. At the end of the incubation period, 10 µl MTT (5 mg/ml) was added and incubated at 37° C. for 1 h. Then, add 200 µl of 100% isopropyl alcohol in all the wells and keep it at rt for 4 h. The reading was taking at 490 nm by using a plate reader (Model SPECTRA max PLUS384 from Molecular Devices, USA). In positive control there was no inhibitor added in the wells and in negative controls only medium was used instead of culture. Here, the values obtained from positive and negative controls are considered to have 100% and 0% equivalent growth of the cells respectively. (FIG. 2)

CONCLUSION

A general protocol for the stereoselective synthesis of α- and β-10-undecenyl C-arabinofuranosides has been developed and the corresponding Motif C disaccharide analogs of cell wall of Mtb are synthesized. The anti-mycobacterial activity of these compounds was evaluated against the *M. Bovis* BCG. One of the C-arabinofuranosides (compound of formula 2) was found to be having the MIC similar to that of frontline anti-tubercular drug ethambutol. [Mikusova, K., Slayden, R. A., Besra, G. S. & Brennan, P. J. *Antimicrob. Agents Chemother.* 1995, 39, 2484-2489].

Advantages of the Invention

This disclosure reveals the promising anti-mycobacterial activity of 10-undecenyl C-☐/☐-arabinofuranosides and of corresponding motif C (of cell wall AG complex of M.Tb) analogues as potential leads for the further development. Protocols for the stereoselective synthesis of both α- and β-C-arabinofuranosides have been disclosed. Selective glycosylation of 5-OH of a free C-arabinofuranoside employing glyclosyl phosphate as a donor has been developed. The α-C-glycoside (IC$_{50}$=0.2 ☐ g/ml) was found to be better inhibitor of *Mycobacterium* than the corresponding β-glycoside (IC$_{50}$=1.1 ☐ g/ml). One of the 2,3-di-O-benzyl derivative has turned to be the best candidate amongst the various compounds screened. To highlight, the ☐-C-glycosides are found to be inhibiting as good as that of ethambutol and are non-cytotoxic to Thp-1 cells at 100 ☐ g/ml concentration. This promising anti-mycobacterial activity and the appealing non-cytotoxicity of these C-glycoside makes them as potential candidates to further investigate.

We claim:
1. A compound of general Formula (II)

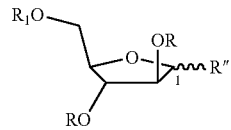

(II)

wherein, R" represents 10-undecenyl;
R$_1$ represents hydrogen or α-D-Arabinofuranosyl or β-D-Arabinofuranosyl of Formula (A")

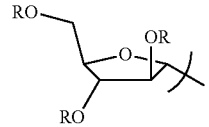

(A")

R in the general Formula (II) and in (A") is selected independently from the group consisting of hydrogen, acetyl, benzyl, alkoxy, methane sulfonyl, carboxyl, unsubstituted or substituted phenyl as given below:

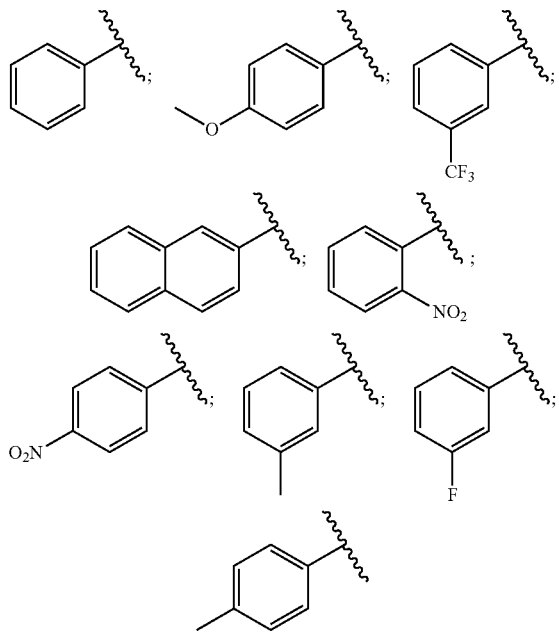

alkyl, alkenyl, alkynyl, and heterocycles.
2. The compound of general formula (II) as claimed in claim 1 wherein representative compounds are:

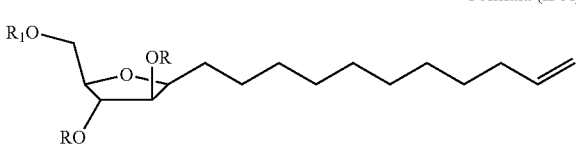

Formula (II-A)

wherein C1 is in β configuration

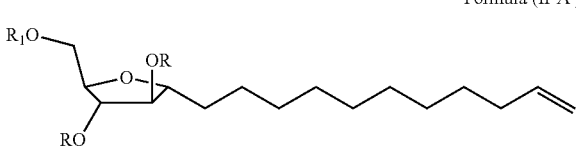

Formula (II-A')

wherein C1 is in α configuration;
R and $R_1$ are as defined in claim 1.

3. The compound as claimed in claim 1 or 2, wherein the compound is selected from the group consisting of:
10-β-D-Arabinofuranosylundecene (1);
10-α-D-Arabinofuranosylundecene (2);
α-D-Arabinofuranosyl-(1→5)-10-β-D-arabinofuranosylundecene (3);
α-D-arabinofuranosyl-(1→5)-10-α-D-arabinofuranosylundecene (4);
2,3-Di-O-benzyl-10-α-D-Arabinofuranosylundecene (16);
α-D-Arabinofuranosyl-(1→5)-2,3-Di-O-benzyl-10-α-D-Arabinofuranosylundecene (17);
2,3-Di-O-phenyl-10-α-D-Arabinofuranosylundecene (18);
2,3-Di-O-(4-methyoxy phenyl)-10-α-D-Arabinofuranosylundecene (19);
2,3-Di-O-(1-naphthyl)-10-α-D-Arabinofuranosylundecene (20);
2,3-Di-O-(3-nitrophenyl)-10-α-D-Arabinofuranosylundecene (21);
2,3-Di-O-(4-nitro phenyl)-10-α-D-Arabinofuranosylundecene (22);
2,3-Di-O-(3-methyl phenyl)-10-α-D-Arabinofuranosylundecene (23);
2,3-Di-O-(4-methyl phenyl)-10-α-D-Arabinofuranosylundecene (24);
2,3-Di-O-(3-flurophenyl)-10-α-D-Arabinofuranosylundecene (25);
2,3-Di-O-methyl-10-α-D-Arabinofuranosylundecene (26);
2,3-Di-O-octyl-10-α-D-Arabinofuranosylundecene (27);
2,3-Di-O-benzyl-10-β-D-Arabinofuranosylundecene (29);
2,3-Di-O-phenyl-10-β-D-Arabinofuranosylundecene (30);
2,3-Di-O-(4-methyoxy phenyl)-10-β-D-Arabinofuranosylundecene (31);
2,3-Di-O-(1-naphthyl)-10-β-D-Arabinofuranosylundecene (32);
2,3-Di-O-(3-nitrophenyl)-10-β-D-Arabinofuranosylundecene (33);
2,3-Di-O-(4-nitro phenyl)-10-β-D-Arabinofuranosylundecene (34);
2,3-Di-O-(3-methyl phenyl)-10-β-D-Arabinofuranosylundecene (35);
2,3-Di-O-(4-methyl phenyl)-10-β-D-Arabinofuranosylundecene (36);
2,3-Di-O-(3-flurophenyl)-10-β-D-Arabinofuranosylundecene (37);
2,3-Di-O-methyl-10-β-D-Arabinofuranosylundecene (38); and
2,3-Di-O-octyl-10-β-D-Arabinofuranosylundecene (39).

4. A process for the preparation of compounds of formula (II) as claimed in claim 1 comprising the steps of:
i. reacting an aldehyde (7) or an epoxide (12) with a grignard reagent in presence of copper catalyst and a solvent to obtain the alcohol (9) or (8) or mixture thereof;

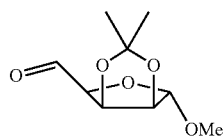

7

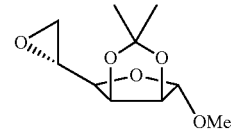

12

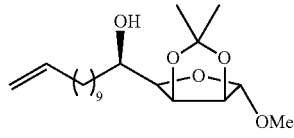

8

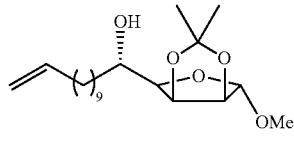

9 ii. mesylating alcohol (9) or (8) as obtained in step (i) followed by acid mediated ring transposition to obtain acetals (11) or (5);

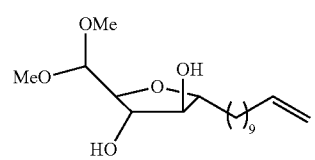

11

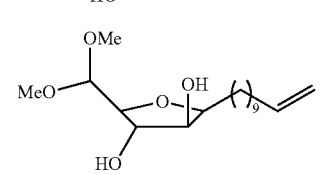

5 iii. hydrolysing the acetals as obtained in step (ii) in presence of aqueous acid and subsequent reduction with alkali metal borohydride in a $C_1$-$C_4$ alcohol of the intermediate aldehyde to obtain compound of formula (1) or (2);

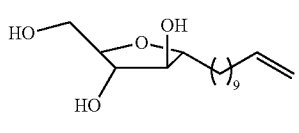

2

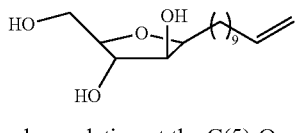

1 iv. selective glycosylating at the C(5)-O— of compounds of formula (1) and (2) followed by debenzoylation to obtain dissachardes (3) and (4);

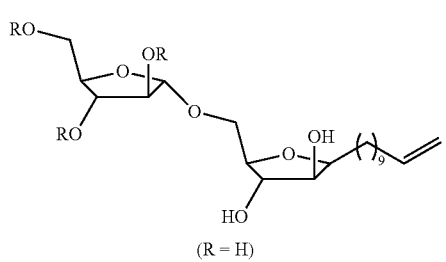

3

(R = H)

-continued

4

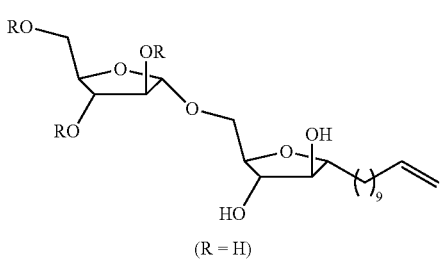

(R = H)

v. alkylation or arylation of compounds of formula (5) and (11) or (3) and (4) followed by hydrolysis and subsequent reduction to obtain compounds of formula (II).

5. The process as claimed in claim 4, wherein Grignard reagent used is selected from the group consisting of 9-decenyl-magnesium bromide or 10-undecenyl magnesium bromide.

6. The process as claimed in claim 4, wherein the copper catalyst is selected from the group consisting of copper powder, Cu(II) halides, copper cyanide, and copper triflate.

7. The process as claimed in claim 4, wherein the solvent used is selected from group consisting of diethyl ether, acetonitrile, THF or DMF.

8. The process for alkylation or arylation at C2 and C3 position of α-acetals (5) and (11) or disaccharides (3) and (4) as claimed in claim 5 wherein said process comprising the steps of:
  a. reacting acetals (5) and (11) or disaccharides (3) and (4) with corresponding alkyl halide R—X or aryl halide Ar—X in presence of sodium hydride or in presence of copper catalyst to obtain dialkyl or diaryl compounds; wherein R is selected independently from the group consisting of alkyl, alkenyl, alkynyl, benzyl, and unsubstituted or substituted phenyl as given below:

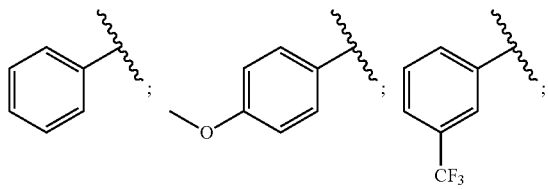

-continued

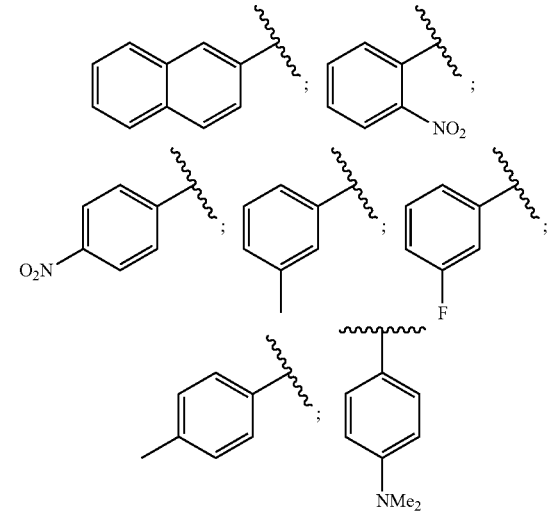

b. hydrolysing dialkyl or diaryl compounds using aqueous Trifluoroacetic acid (TFA) and subsequent reduction with alkali metal borohydride in a $C_1$-$C_4$ alcohol to obtain alkylated or arylated compounds.

9. A pharmaceutical composition comprising the antimycobacterial compounds of Formula (II) according to claim 1, in association with at least one pharmaceutically acceptable excipient.

10. A method for treating tuberculosis in a subject, comprising administering to the subject an effective amount of at least one compound of Formula (II) in association with at least one pharmaceutical excipient.

11. A compound that is 10-α-D-Arabinofuranosylundecane (28) or 10-β-D-Arabinofuranosylundecane (40).

12. The process as claimed in claim 6, wherein the copper catalyst is copper cyanide.

13. The process as claimed in claim 8, wherein the $C_1$-$C_4$ alcohol is step (b) is isopropanol.

* * * * *